United States Patent
Sunazuka et al.

(10) Patent No.: US 9,789,021 B2
(45) Date of Patent: Oct. 17, 2017

(54) MEDICAL IMAGING APPARATUS, BED FOR MEDICAL IMAGING APPARATUS, AND PEDAL UNIT

(71) Applicants: Izumi Sunazuka, Tokyo (JP); Satoshi Iizuka, Tokyo (JP)

(72) Inventors: Izumi Sunazuka, Tokyo (JP); Satoshi Iizuka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 748 days.

(21) Appl. No.: 14/354,642

(22) PCT Filed: Nov. 14, 2012

(86) PCT No.: PCT/JP2012/079462
§ 371 (c)(1),
(2) Date: Apr. 28, 2014

(87) PCT Pub. No.: WO2013/073552
PCT Pub. Date: May 23, 2013

(65) Prior Publication Data
US 2014/0303477 A1    Oct. 9, 2014

(30) Foreign Application Priority Data
Nov. 18, 2011    (JP) .................. 2011-252300

(51) Int. Cl.
*A61B 5/05*    (2006.01)
*A61G 13/10*    (2006.01)
(Continued)

(52) U.S. Cl.
CPC ............ *A61G 13/10* (2013.01); *A61B 5/0555* (2013.01); *A61B 6/032* (2013.01); *A61B 6/035* (2013.01);
(Continued)

(58) Field of Classification Search
CPC ........ A61G 13/10; A61B 6/032; A61B 6/035; A61B 6/0407; A61B 6/4411; A61B 6/467; A61B 5/0555; A61B 6/0457
(Continued)

(56) References Cited

U.S. PATENT DOCUMENTS

| 4,671,728 A | 6/1987 | Clark et al. |
| 6,352,240 B1 * | 3/2002 | Eckstein ................ A61G 7/018 |
| | | 137/636.1 |

(Continued)

FOREIGN PATENT DOCUMENTS

| JP | 62-14842 | 1/1987 |
| JP | 2005-508691 | 4/2005 |

OTHER PUBLICATIONS

International Search Report in PCT/JP2012/079462.

*Primary Examiner* — Sanjay Cattungal
(74) *Attorney, Agent, or Firm* — Cooper & Dunham LLP

(57) ABSTRACT

Realized is a pedal mechanism that does not lock and does not provide an operation feeling unless operated in a determined order. The pedal mechanism has first and second pedals 105 and 106, first and second plates 108 and 109, and a locking bar 115. The radius of the second plate 109 is smaller than that of the first plate 108, and the second plate does not come into contact with the locking bar in a state where a circular-arc region of the first plate supports the locking bar 115. Therefore, the second pedal does not give an operation feeling even when stepped on, and the second plate cannot be locked. In a locked state where the locking bar is located in a cutout region of the first plate, the locking bar contacts the second plate, the second pedal provides an operation feeling, and the second plate can be locked.

12 Claims, 23 Drawing Sheets

(51) Int. Cl.
*A61B 5/055* (2006.01)
*A61B 6/03* (2006.01)
*A61B 6/04* (2006.01)
*A61B 6/00* (2006.01)

(52) U.S. Cl.
CPC .......... *A61B 6/0407* (2013.01); *A61B 6/4411* (2013.01); *A61B 6/467* (2013.01); *A61B 6/0457* (2013.01)

(58) Field of Classification Search
USPC ............................... 600/407–480; 5/600–618
See application file for complete search history.

(56) References Cited

U.S. PATENT DOCUMENTS

| | | | |
|---|---|---|---|
| 2001/0019602 A1* | 9/2001 | Nakajo | G03B 42/025 378/209 |
| 2005/0020906 A1 | 1/2005 | Seijger et al. | |
| 2005/0034237 A1* | 2/2005 | Lenting | A61B 6/0457 5/600 |
| 2005/0172405 A1* | 8/2005 | Menkedick | A61B 5/1115 5/618 |
| 2008/0289108 A1* | 11/2008 | Menkedick | A61G 7/0528 5/610 |
| 2009/0049610 A1* | 2/2009 | Heimbrock | A61G 7/008 5/600 |
| 2014/0026322 A1* | 1/2014 | Bell | A61G 7/00 5/600 |
| 2014/0259410 A1* | 9/2014 | Zerhusen | A61G 7/00 5/600 |
| 2014/0296692 A1* | 10/2014 | Iizuka | A61B 5/0555 600/407 |
| 2015/0281659 A1* | 10/2015 | Hood | A61G 7/018 348/143 |
| 2016/0193095 A1* | 7/2016 | Roussy | A61G 7/002 5/11 |

* cited by examiner

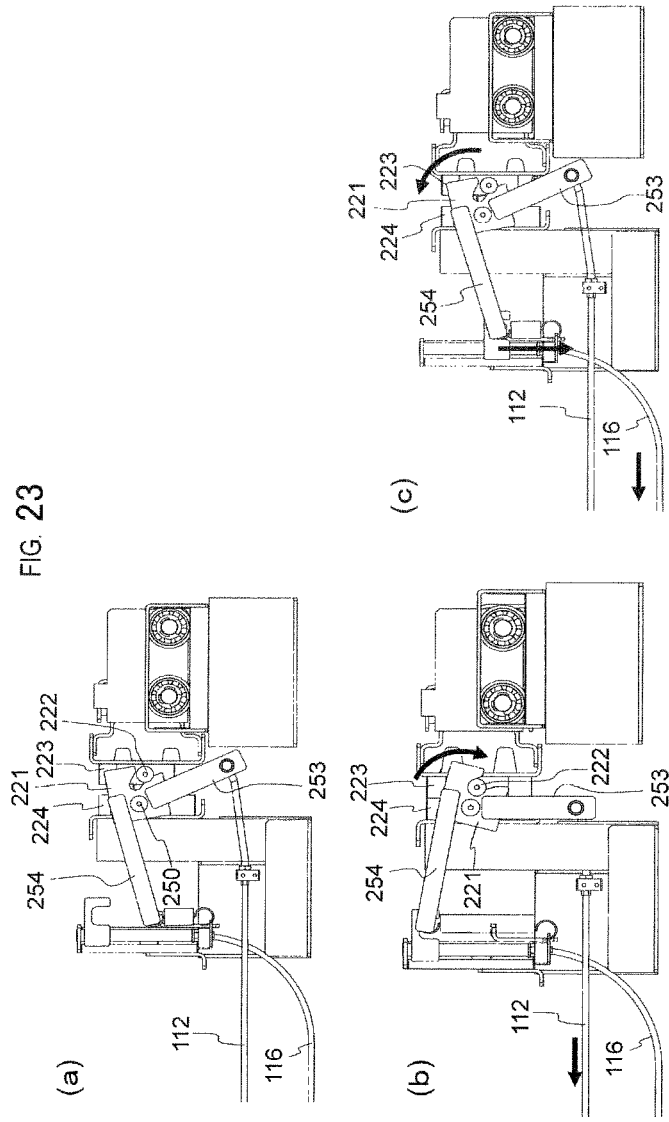

MEDICAL IMAGING APPARATUS, BED FOR MEDICAL IMAGING APPARATUS, AND PEDAL UNIT

TECHNICAL FIELD

The present invention relates to a medical imaging apparatus, and particularly, to a bed that is attachable to and detachable from an apparatus main body.

BACKGROUND ART

Medical imaging apparatuses, such as a magnetic resonance imaging (hereinafter referred to as MRI) apparatus and a CT apparatus, have a structure in which an object is mounted on a bed and the bed is inserted into an imaging space of an apparatus main body. Therefore, the bed has a complicated configuration including a lifting mechanism that lifts a top plate, on which the object is mounted, to the height of the imaging space of the apparatus main body, a horizontal movement mechanism that horizontally moves the top plate in order to insert an imaging site of the object up to the center of the imaging space, a control unit that performs the movement according to a control signal from the apparatus main body, or the like. For this reason, the bed usually has a weight of hundreds of kilograms, is precisely positioned, and is mechanically and electrically connected to the apparatus main body.

In recent years, for an improvement in the throughput of examination for objects, beds that are usable after being separated from the apparatus main body are required. For example, in the case of an object that cannot enter a bed by itself, the work of transporting the object to the vicinity of the bed, lifting the object by two or more examiners, and mounting and fixing the object to the bed is required, and a examiner's burden is great.

Particularly in the case of an MRI apparatus, metallic mobile beds, such as a usual stretcher, are drawn close to the apparatus main body by a strong magnetic field generated from the apparatus main body. Therefore, the object cannot be transported to the side of a bed fixed to the MRI apparatus by the usual mobile beds.

Therefore, in the related art, an object is transported in a procedure of transferring the object from the usual stretcher to a special stretcher made of a nonmagnetic substance in the lobby of an examination room, and transporting the object to the side of the bed of the MRI apparatus. In this case, a transfer from a bed to the usual stretcher, a transfer from the usual stretcher to the nonmagnetic stretcher, and a transfer from the nonmagnetic stretcher to the bed of the MRI apparatus are required, and the number of transfer times is three.

Therefore, if the bed of the MRI apparatus can be separated from the main body and be pushed with the hands and moved to the lobby of the examination room or the bedside of an object, and the object can be directly transferred from the usual stretcher or bed to the bed of the MRI apparatus, the number of times of transfer can be reduced. Accordingly, not only can an improvement in the throughput of examination be realized, but also a burden on the object can be reduced.

A bed that is attachable to and detachable from a main body of an MRI apparatus is disclosed in PTL 1. In this technique, as shown in FIGS. 1 to 5 of PTL 1, a front lower portion of the apparatus main body is equipped with a docking mechanism 16, such as a guide 24 having a conical outer shape. Meanwhile, a lower portion of a front end of a bed is equipped with a coupling mechanism to be coupled to the docking mechanism 16. When the bed is coupled to the apparatus main body, the bed is brought close to the apparatus main body until a lateral plate 100 arranged at a front end portion of the bed bumps against docking points 32 and 34 on both sides of an upper portion of the conical guide 24 of the apparatus main body. The movement of the bed at this time is guided as a pair of pins 96 and 98 below the lateral plate 100 are inserted so as to run along the conical guide 24 of the apparatus main body. If the lateral plate 100 of the bed bumps against the docking point 32, the bed is fixed to the apparatus main body by coupling a latch hook 58 of a lower portion of the bed to a pin member 56 at the tip of the conical guide 24 of the apparatus main body.

CITATION LIST

Patent Literature

[PTL 1] Specification of U.S. Pat. No. 4,567,894

SUMMARY OF INVENTION

Technical Problem

As described above, the bed moves the imaging site of the object to the center of the imaging space under the control of a control device of the medical imaging apparatus. For this reason, when the bed that is movable after being separated from the apparatus main body is docked with the apparatus main body, it is necessary not only to mechanically couple the bed to the apparatus main body, but also to electrically connect a plurality of signal lines of the bed to a plurality of signal lines of the main body.

Since the docking mechanism described in PTL 1 is a docking mechanism that performs mechanical docking, electrical docking cannot be performed by the mechanism of PTL 1. Usually, the electrical docking is performed by means such as inserting connectors with the hands, and user-friendliness is low. Since the number of the signal lines that couple the apparatus main body of the MRI apparatus and the bed are several tens or more and the number is large, large-sized connectors are required in order to couple these lines using the connectors. Since the large-sized connectors require a force when being connected with the hands and are limited in terms of a space where the connector can be arranged, connection operation becomes difficult.

Therefore, it is possible to adopt a configuration in which the connectors are mechanistically connected. For example, it is considered that a mechanism moving the connectors for coupling therebetween is arranged around the connectors, and the connectors are coupled together face to face through the operation of this mechanism. However, when the mechanism is operated in a state where a connector on a bed side and a connector on an apparatus main body side have positionally deviated, there is a risk that the connectors may collide with each other and damage the connector pins, in a state where the connectors have positionally deviated. In order to prevent this, it is necessary to adopt an operating procedure in which, first, the bed and the apparatus main body are positioned and mechanically docked with each other, and thereafter, a mechanism that performs electrical docking is operated to electrically connect the connectors.

Thus, an operating mechanism that can cancel out the operation and allows an operator to notice an error is required when the operating procedure is erroneous.

An object of the invention is to realize a pedal mechanism that does not lock and does not provide an operation feeling unless operated in a determined order.

Solution to Problem

In order to achieve the above object, the invention has the following structure. That is, the medical imaging apparatus has a bed that mounts an object, a main body that images the object, and a pedal unit that is provided at the bed to operate the bed. A pedal unit has first and second pedals, a first plate that rotates through the operation of the first pedal, a second plate that rotates through the operation of the second pedal, and a locking bar that is arranged so as to be capable of being in contact with outer peripheries of the first and second plates.

Central axes of rotation of the first plate and the second plate are coaxial. The first plate has a circular-arc region with a radius r1 from the central axis and a cutout region with a distance r2 from the central axis smaller than the radius r1, at an outer periphery thereof.

The second plate has a circular-arc region with a radius from a central axis equal to the distance r2 at an outer periphery thereof. The second plate does not come into contact with the locking bar in a state where the circular-arc region of the first plate supports the locking bar through the operation of the first pedal. The second plate rotates while contacting the locking bar through the operation of the second pedal, in a locked state where the locking bar is located in the cutout region of the first plate.

Advantageous Effects of Invention

According to the invention, the second plate does not come into contact with the locking bar and does not provide an operation feeling if the locking bar is inserted into and is not locked into the cutout region of the first plate. Hence, it is possible to realize a pedal mechanism that does not lock and does not provide an operation feeling unless operated in the order of the first pedal and the second pedal.

BRIEF DESCRIPTION OF DRAWINGS

FIGS. 23(a), 23(b), and 23(c) are side views showing a coupling operation of electric connectors 223 and 224 of docking units 4 and 5 of the medical imaging apparatus of FIG. 1.

DESCRIPTION OF EMBODIMENTS

Figure 1:
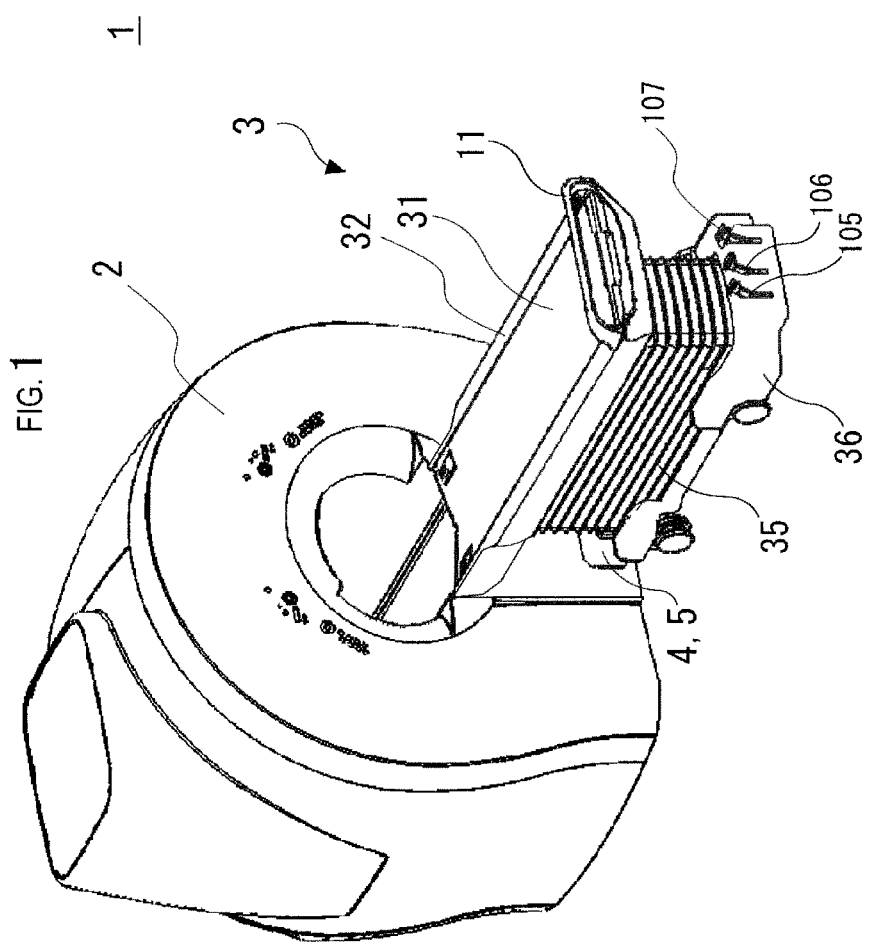
FIG. 1 is a perspective view of a medical imaging apparatus of the present embodiments.

A medical imaging apparatus of the invention has the structure as follows. That is, the medical imaging apparatus has a bed that mounts an object, a main body that images the object, and a pedal unit that is provided at the bed to operate the bed.

The pedal unit has first and second pedals, a first plate that rotates through the operation of the first pedal, a second plate that rotates through the operation of the second pedal, and a locking bar that is arranged so as to be capable of being in contact with outer peripheries of the first and second plates. Central axes of rotation of the first plate and second plate are coaxial. The first plate has a circular-arc region with a radius r1 from the central axis and a cutout region with a distance r2 from the central axis smaller than the radius r1, at an outer periphery thereof. The second plate has a circular-arc region with a radius from the central axis equal to the distance r2 at an outer periphery thereof. The second plate does not come into contact with the locking bar in a state where the circular-arc region of the first plate supports the locking bar through the operation of the first pedal. The second plate rotates while contacting the locking bar through the operation of the second pedal in a locked state where the locking bar is located in the cutout region of the first plate.

It is possible to adopt a configuration in which one end of the first wire and one end of the second wire are connected to the first and second plates, respectively, and the other ends of the first and second wires are respectively connected to members of the bed to be operated.

It is also possible to adopt a configuration in which the pedal unit further includes a third pedal, a release plate that rotates through the operation of the third pedal, and a biasing member that applies a force that pushes the locking bar against the outer peripheries of the first and second plates. In this case, the release plate that has rotated through the operation of the third pedal lifts the locking bar against the force of the biasing member to allow the locking bar to move from the cutout region of the first plate to the circular-arc region.

A configuration may be adopted in which a protrusion is arranged between the circular-arc region and the cutout region at an outer periphery of the first plate, and the locking bar rides over the protrusion from the circular-arc region and moves to the cutout region when the first plate rotates through the operation of the first pedal.

Additionally, a configuration may be adopted in which a locking region with a distance from the central axis equal to the radius r2 of the circular-arc region, and a protrusion arranged between the circular-arc region and the locking region are provided at an outer periphery of the second plate, and the locking bar rides over the protrusion from the circular-arc region and moves to the locking region when the second plate rotates through the operation of the second pedal.

In this case, it is desirable that the distance of the highest portion of the protrusion of the second plate from the central axis be smaller than the radius r1 of the circular-arc region of the first plate.

It is desirable to adopt a configuration in which the release plate unlocks the second plate and the first locking plate in this order.

It is desirable to adopt a configuration in which the first pedal returns to a predetermined initial position without interlocking with the first plate in a locked state where the locking bar is located in the cutout region of the first plate.

It is also possible to adopt a configuration in which one end of a third wire is fixed to the release plate and the other end of the third wire is connected to a member of the bed, the operation of which is to release the bed.

For example, it is possible to adopt a configuration in which the bed is structured to be detachable from the main body, a coupling member that mechanically couples the bed and the main body is connected to the other end of the first wire, and a coupling member that electrically connects the bed and the main body is connected to the other end of the second wire.

Hereinafter, embodiments of the invention will be specifically described with reference to the drawings.

A medical imaging apparatus 1, as shown in FIG. 1, includes an apparatus main body 2 and a bed 3. The main device body 2 may have any configuration as long as an image of a subject mounted on the bed 3 may be captured. For example, a main body of an MRI apparatus or a CT apparatus can be used. Here, a case where the medical imaging apparatus 1 is the MRI apparatus will be described below as an example.

The apparatus main body 2 is configured to include a gantry equipped with a static magnetic field generator that generates a static magnetic field, a gradient magnetic field coil, a radio frequency (RF) magnetic field pulse transmitting coil, and a shim plate, and a gantry cover that covers the gantry. In the example of FIG. 1, the static magnetic field generator of the gantry is in the shape of a cylinder in which an axial direction is made horizontal, and the internal space of the cylinder serves as an imaging space. However, the invention is not limited to the cylindrical static magnetic field generator.

Moreover, the MRI apparatus includes a gradient magnetic field power amplifier that supplies an electric current to the gradient magnetic field coil, a radio frequency power amplifier that supplies a radio frequency signal to the RF magnetic field pulse transmitting coil, a radio frequency amplifying circuit, a computer, an operating unit, and a display, as a power source, control, and signal processing system.

The apparatus main body 2 is arranged in an electromagnetically shielded room, and the power source, control, and signal processing system is arranged outside the electromagnetically shielded room and is electrically connected to the apparatus main body with a cable.

The static magnetic field generator generates a static magnetic field in the imaging space, and the shim plate generates a magnetic field that improves the uniformity of the static magnetic field to a predetermined value or higher. The gradient magnetic field coil generates gradient magnetic fields in predetermined XYZ directions, respectively, in the imaging space. The RF magnetic field pulse transmitting coil transmits an RF magnetic field pulse to the imaging space.

The computer outputs control signals to the gradient magnetic field power amplifier, the radio frequency power amplifier, and the radio frequency amplifying circuit, and controls the application timing and direction of a gradient magnetic field, the irradiation timing of an RF magnetic field pulse, or the like according to a predetermined imaging sequence. Accordingly, the nuclear magnetic-resonance (NMR) signal produced from an object is received by a receiving coil arranged near the object. The radio frequency amplifying circuit detects and amplifies this signal under the control of the computer, and the computer reconstructs an image according to a predetermined image reconstruction program, and displays the image on a display or the like. The operating unit receives imaging conditions or the like from an examiner.

The bed 3 includes a top plate 31 that allows an object to be mounted thereon, a top plate holding portion 32 that holds the top plate 31, a frame that holds the top plate holding portion 32 so as to be vertically movable, a vertical drive unit that vertically moves the top plate holding portion 32, a horizontal drive mechanism that horizontally moves the top plate 31 with respect to the top plate holding portion 32, a horizontal drive unit that drives the horizontal drive mechanism, four wheels 33 that are attached to a lower portion of the frame, and bellows portions 35 and a cover 36 that cover an outer periphery of the frame, and a handle portion 11. By virtue of these configurations, the bed 3 can be inserted into an imaging region by raising the top plate 31 to the height of the imaging space of the gantry of the apparatus main body 2 and making the top plate 31 slide horizontally with respect to the top plate holding portion 32. This allows an imaging site of an object to be transported to the center of the imaging space.

Figure 2:
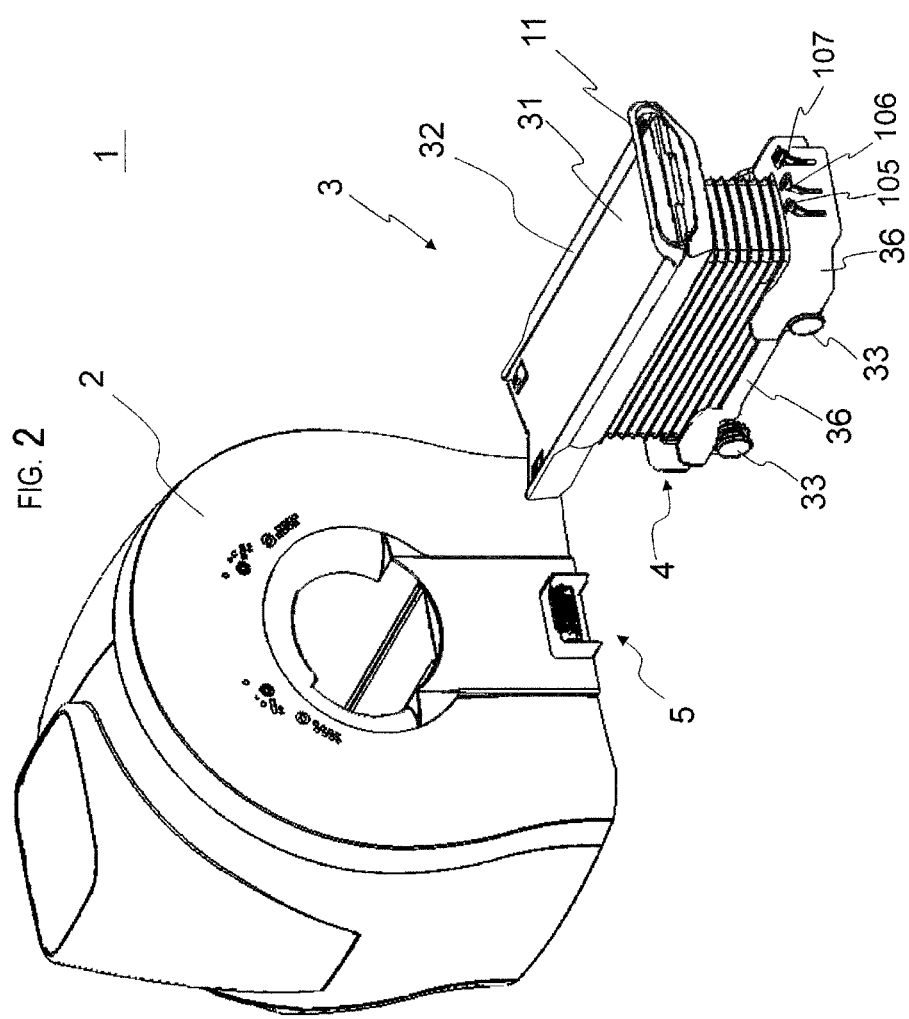
FIG. 2 is a perspective view of the state of the medical imaging apparatus of FIG. 1 where a bed 3 is separated from an apparatus main body 2.

In the invention, the bed 3 is attachable to and detachable from the apparatus main body 2. An object can be mounted on the bed by pushing the handle portion 11 of the bed 3 separated from the apparatus main body 2 as shown in FIG. 2 with his/her hands and moving the bed to a lobby, a hospital room of the object, or the like where the magnetism of the apparatus main body 2 does not reach. After the mounting, the bed can be docked with the apparatus main body 2 as shown in FIG. 1 in a state where the object is mounted.

A front end portion of the bed 3 and a front surface of the apparatus main body 2 are respectively equipped with docking units 4 and 5 as the coupling mechanisms. As the docking units 4 and 5 are fitted to each other, the bed 3 is mechanically coupled to the apparatus main body 2. Additionally, the electric connectors and mechanism units are respectively arranged within the docking units 4 and 5. After the docking units 4 and 5 are mechanically coupled, the electric connector within the docking unit 4 is coupled to and is electrically connected to the electric connector within the docking unit 5 through the operation of the mechanism units of the electric connectors.

Three pedals 105, 106, and 107 are installed at a rear end portion of the bed 3. The pedal 105 is a pedal for performing the operation of coupling the hook in the docking unit 4 to the coupling bar within the docking unit 5 to complete mechanical docking after the docking units 4 and 5 are fitted to each other. The pedal 106 is a pedal for performing the operation of coupling the electric connectors arranged within the docking unit 4 and 5, respectively, after the completion of the mechanical docking.

It is necessary to perform the operation of the pedal 105 and the operation of the pedal 106 in this order. That is, first, the bed 3 is moved and coupled to the apparatus main body 2, the pedal 105 is operated to latch the hook within the docking unit 4 to the coupling bar of the docking unit 5, and the mechanical docking is completed. The electric connector on the bed 3 side and the electric connector on the apparatus main body 2 side are coupled together by operating the pedal 106 after the electric connector of the bed 3 is aligned with the electric connector of the apparatus main body 2 by this mechanical docking.

In the invention, a configuration in which an operation is not received if the operation is not an operation in the order of the pedal 105 and the pedal 106 is realized by the mechanism units of the pedals 105 and 106.

Meanwhile, the pedal 107 is a pedal for causing decoupling of the electric connectors and releasing of the hook for mechanical docking to be performed in this order.

Figure 3:
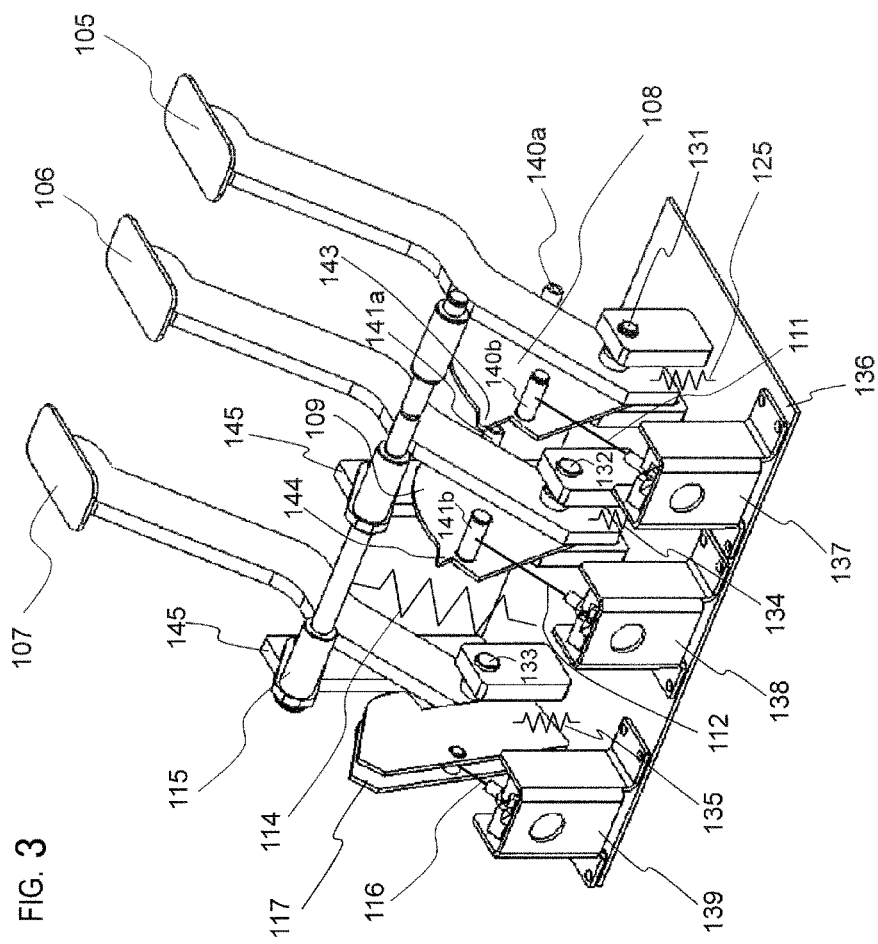
FIG. 3 is a perspective view of a pedal unit of the bed of the embodiments.

The pedals 105 to 107 and the mechanism units thereof in the first embodiment will be described in detail. The pedals 105 to 107 and the mechanism units thereof constitute the pedal unit 104. FIG. 3 is a perspective view of the pedal unit 104. It should be noted that the shape of springs 114, 125, 134, and 135 or the like is drawn in a simplified manner in FIG. 3.

The pedal unit 104, as shown in FIG. 3, includes the three types of pedals 105 to 107, a substantially fan-shaped locking plate A (first plate) 108, a substantially fan-shaped locking plate B (second plate) 109, and a release plate 117, a locking bar 115, wires A 111, B 112 and C 116, wire guides 137 to 139, and a supporting plate 136 that mounts these. The supporting plate 136 is fixed to the frame of the bed 3.

The pedals 105 to 107 have upper ends exposed to the outside of the cover 36 of the bed 3, and respectively turn with shafts 131 to 133 as supporting points, as an operator steps on the upper ends with his/her foot. The shafts 131 to 133 are arranged so that central axes thereof coincide with each other. The locking plate A 108 and the locking plate B 109 are rotatably attached to the shafts 131 and 132 of the pedals 105 and 106, respectively. In the locking plate A 108 and the locking plate B 109, pedal-receiving shafts 140a and 141a are arranged at end portions in a circumferential direction, and shafts 140b and 141b for wire connection are arranged at end portions in the circumferential direction. When the pedals 105 and 106 are stepped on and turned, the pedals 105 and 106 push the pedal-receiving shafts 140a and 141b of the locking plate A 108 and the locking plate B 109, respectively; therefore, the locking plate A 108 and the locking plate B 109 are also configured to rotate. End portions of the wires A 111 and B 112 are fixed to the shafts 140b and 141b, respectively, for wire connection.

The release plate 117 is fixed to the shaft 133 of the pedal 107, and rotates in conjunction with the turning of the pedal 107. An end portion of the wire C 116 is fixed to the release plate 117.

Ends of springs 125 and 134 on one side are fixed to the pedals 105 and 106, respectively, and the other ends of the springs 125 and 134 are fixed to the supporting plate 136. The springs 125 and 134 are biased in a direction in which the spring returns to initial positions (positions of FIG. 3) thereof from a case where the pedals 105 and 106 are stepped on and turned by an examiner. Additionally, the pedal 107 and the release plate 117 that are coaxially fixed are biased in a direction in which the pedal and the release plate return to initial positions (positions of FIG. 3) thereof by a spring 135 attached to the release plate 117.

Figure 4:
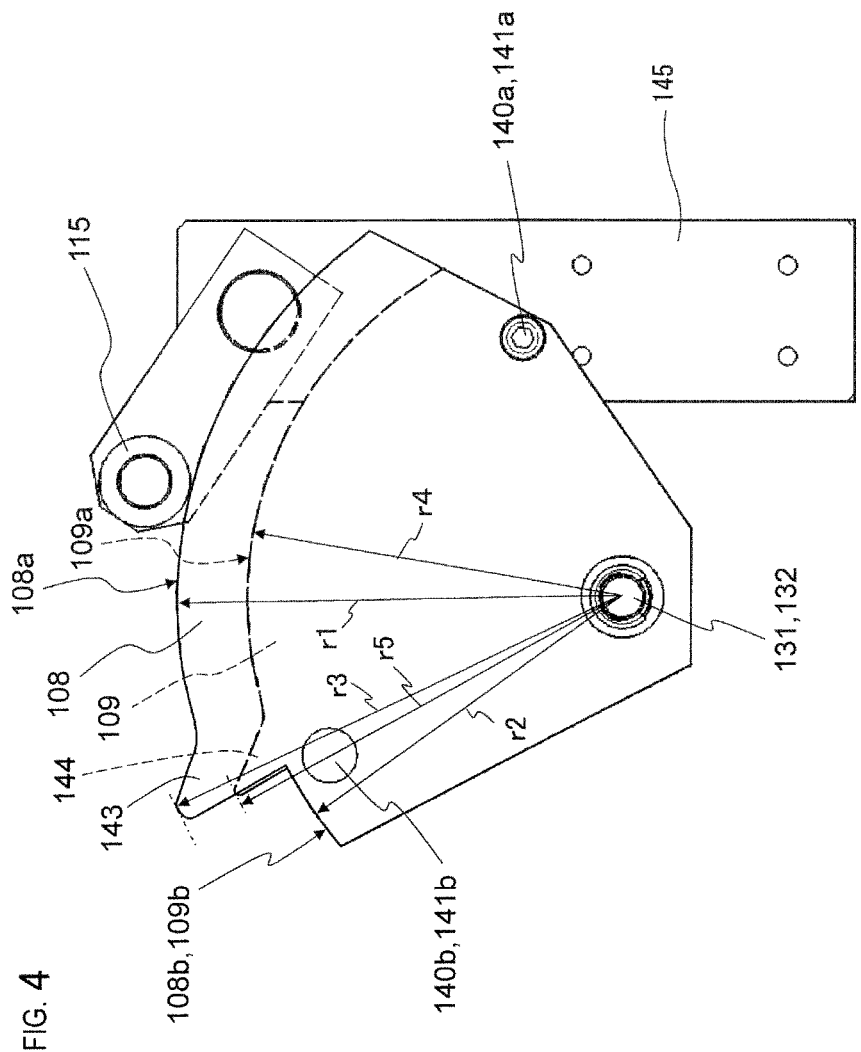
FIG. 4 is a side view of locking plates A 108 and B 109 of the pedal unit of FIG. 3.

The substantially fan-shaped locking plate A 108 and locking plate B 109 include protrusions 143 and 144 at the same positions of outer peripheries thereof near the shafts 140b and 141b for wire connection, as shown in a side view of FIG. 4. In the locking plate A 108, the radius r1 of a circular-arc region 108a closer to the pedal-receiving shaft 140a side than the protrusion 143 is greater than the radius r2 of a cutout region 108b closer to the shaft 140b side for wire connection than the protrusion 143. The radius r3 of the highest position of the protrusion 143 is greater than the radius r1. In addition, in the present embodiment, an outer periphery of the cutout region 108b is also formed in the shape of a circular arc. However, the outer periphery may be linear without being limited to the circular-arc shape.

Meanwhile, in the locking plate B 109, the radius of a circular-arc region 109a closer to the side of the shaft 141b for wire connection than the protrusion 144 coincides with the radius r2 of a cutoff region 108b closer to the side of the shaft 140b for wire connection than the protrusion 143 of the locking plate A 108. The radius r4 of the locking plate B 109 on the pedal-receiving shaft 141a side is the same as the radius r2 of this locking plate closer to the shaft 141b for wire connection than the protrusion 144. The radius r5 of the highest position of the protrusion 144 is smaller than the radius r1. In addition, in the present embodiment, an outer periphery of the locking region 109*b* is also formed in the shape of a circular arc. However, the outer periphery may be linear without being limited to the circular-arc shape.

That is, in FIG. 4, the respective radii are designed so as to satisfy a relationship of r3>r1>r5>r4=r2.

Additionally, the side surfaces of the protrusions 143 and 144 on the pedal-receiving shaft 141*a* side incline with respect to the radial direction, and the side surfaces of the protrusions on the opposite side have a steeply rising shape that coincides with the radial direction.

The release plate 117 has a tip shape that inclines in order to push up the locking bar 115 against the force of the spring 114.

The locking bar 115 is arranged so as to stretch over the release plate 117, the locking plate A 108 and the locking plate B 109, and is supported by supporting portion 145. Tips of the supporting portions 145 are equipped with moving parts that make the supporting position of the locking bar 115 movable. Additionally, a spring 114 is attached to the locking bar 115, and is biased so as to be pushed against the outer peripheries of the locking plate A 108 and the locking plate B 109 or the tip of the release plate 117. In an initial state (FIG. 3), the locking bar 115 is in contact with the circular-arc region 108*a* (radius r1) of the locking plate A 108 with the largest radius, and is therefore not in contact with the locking plate B 109. The locking bar 115 includes rollers in the portions that contact the outer peripheries of the locking plate A 108 and the locking plate B 109 or the tip of the release plate 117, respectively.

Figure 5:
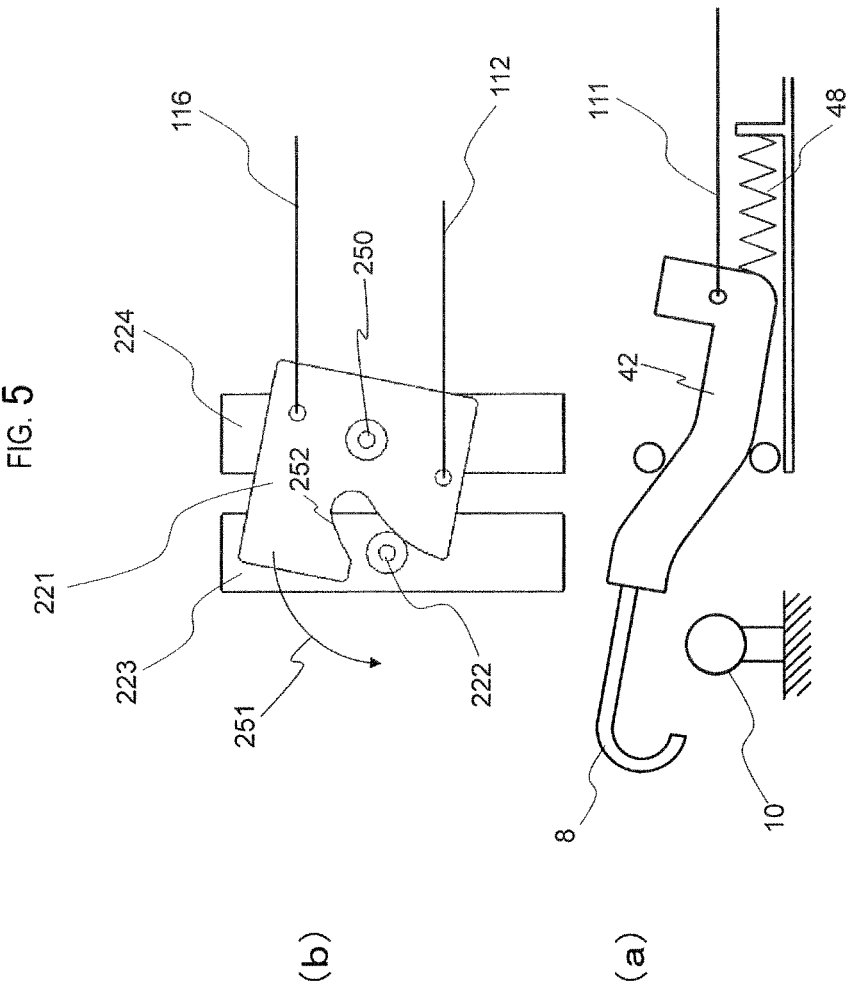
FIG. 5(a) is a simplified explanatory view showing a hook 8 of the docking unit 4 of the bed 3 of the embodiments, and a coupling bar 10 of a docking unit 5 of the apparatus main body 2.
FIG. 5(b) is a simplified explanatory view showing an electric connector 224 and a coupling tool 221 of the docking unit 4 of the bed 3 of the embodiments, and an electric connector 223 and pins 222 of the docking unit 5 of the apparatus main body 2.

As shown in FIG. 5(*a*), the hook 8 arranged within the docking unit 4 of the bed 3 is connected to the tip of the wire A 111. Meanwhile, as shown in FIG. 5(*b*), the coupling tools 221 of the electric connector 224 arranged within the docking unit 4 of the bed 3 are connected to the tips of the wires B 112 and C 116. As the coupling tools 221 are pulled by the wire B 112 and are rotated in a direction of arrow 251 around a shaft 250, projections (pins) 222 of the electric connector 223 arranged within the docking unit 5 of the apparatus main body 2 are pulled into recesses 252, thereby coupling the electric connectors 223 and 224 together. In contrast, as the wire C 116 is pulled and the coupling tools are rotated around the shaft 250 in a direction opposite to the direction of the arrow 251, the coupling is released. FIGS. 5(*a*) and 5(*b*) are shown in a simplified manner in order to simplify description. Specific structures will be described below.

Figure 6:
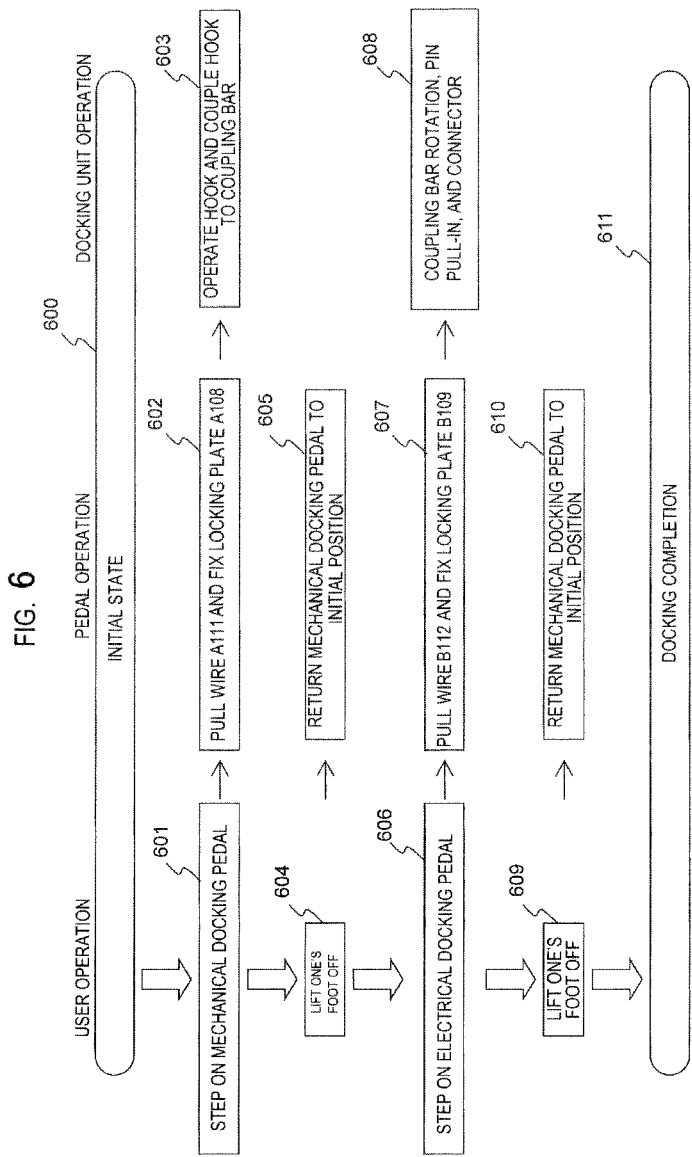
FIG. 6 is a block diagram showing the flow of operation for mechanically and electrically connecting the bed 3 of the embodiments to the apparatus main body.
Figure 7:
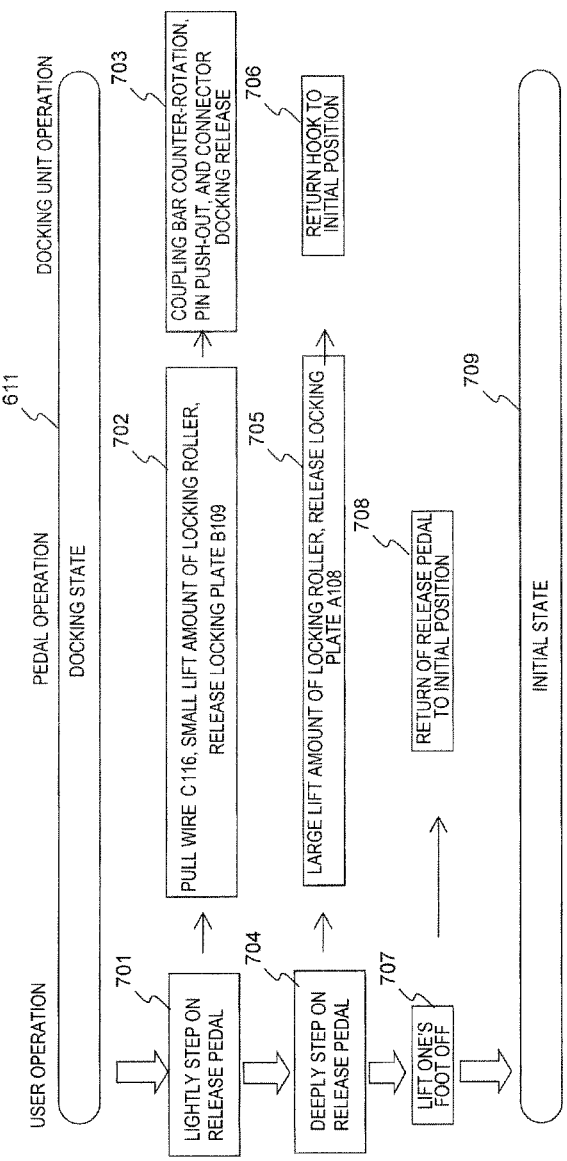
FIG. 7 is a block diagram showing the flow of operation for mechanically and electrically disconnecting the bed 3 of the embodiments from the apparatus main body.

The operation of the pedal unit 104 during the docking and separation of the bed 3 to/from the apparatus main body 2 will be described with reference to FIGS. 6 and 7. FIG. 6 is a block diagram showing the flow of the pedal operation during docking, and FIG. 7 is a block diagram showing the flow of the pedal operation during separation. In FIGS. 6 and 7, an operation performed by an operator is shown in a left column, the operation of a pedal is shown in a middle column, and the operation of the hook connector is shown in a right column.

During docking, an examiner holds the handle portion 11 of the bed 3 to move the bed toward the apparatus main body 2, and a docking mechanism within the docking unit 4 is inserted into a docking mechanism within the docking unit 5 of the apparatus main body 2. Accordingly, the bed 3 stops at the position where the bed 3 is coupled to the apparatus main body 2 as shown in FIG. 1. In this state, the pedal unit 104 is in the initial state of FIG. 3.

Figure 8:
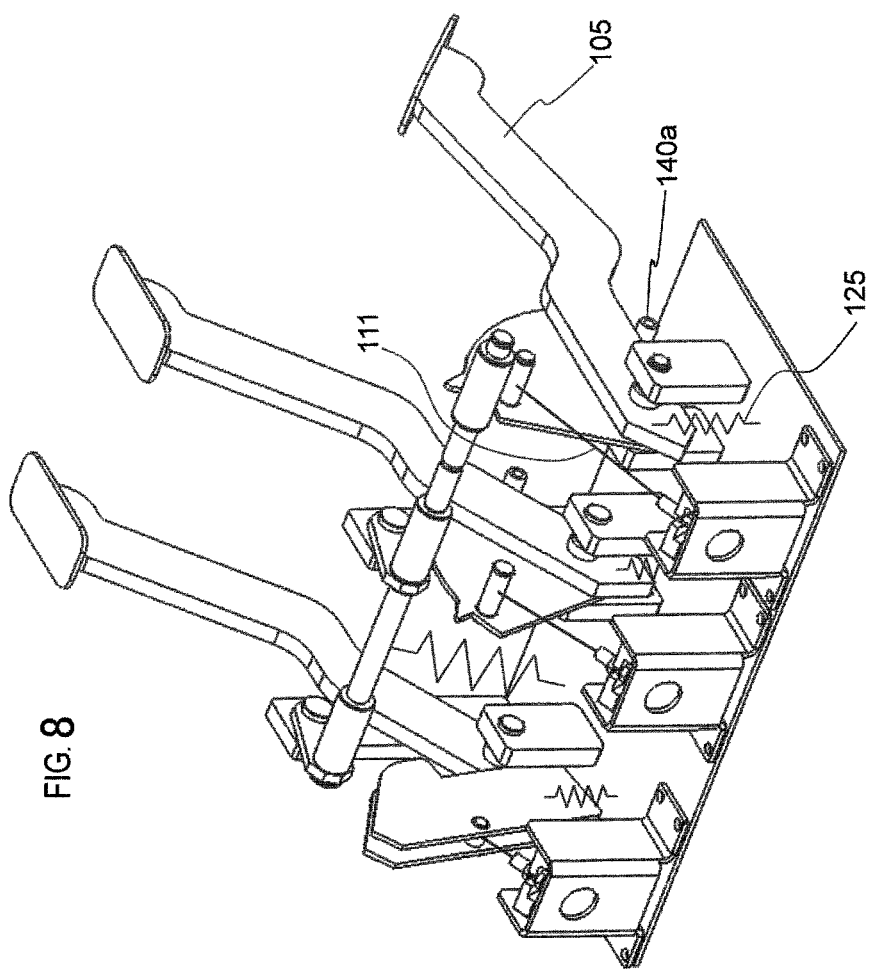
FIG. 8 is a perspective view of a state where a pedal 105 of the pedal unit of FIG. 3 is stepped on, and the locking plate A 108 is locked to a locking bar 115.

In the pedal unit 104, first, the examiner steps on the mechanical docking pedal 105 as shown in FIG. 8 (Step 601 of FIG. 6). Through this operation, the pedal-receiving shaft 140*a* is pushed by the pedal 105, the locking plate A 108 rotates together with the pedal 105, and the wire A 111 is pulled.

At this time, the locking bar 115 contacts the circular-arc region 108*a* of the locking plate A 108 with the radius r1. If the locking plate A 108 is rotated until the protrusion 143 comes to the position of the locking bar 115, and the locking plate A 108 is further rotated, the locking bar 115 rides over the protrusion 143 and the radius r2 (<r1) of the locking plate A 108 reaches the cutout region 108*b*. Unless the locking bar 115 is pushed up by the release plate 117, the locking bar cannot return while riding over the steeply rising side surface shape of the protrusion 143, and the locking plate A 108 is locked by the locking bar 115 (Step 602).

Figure 9:
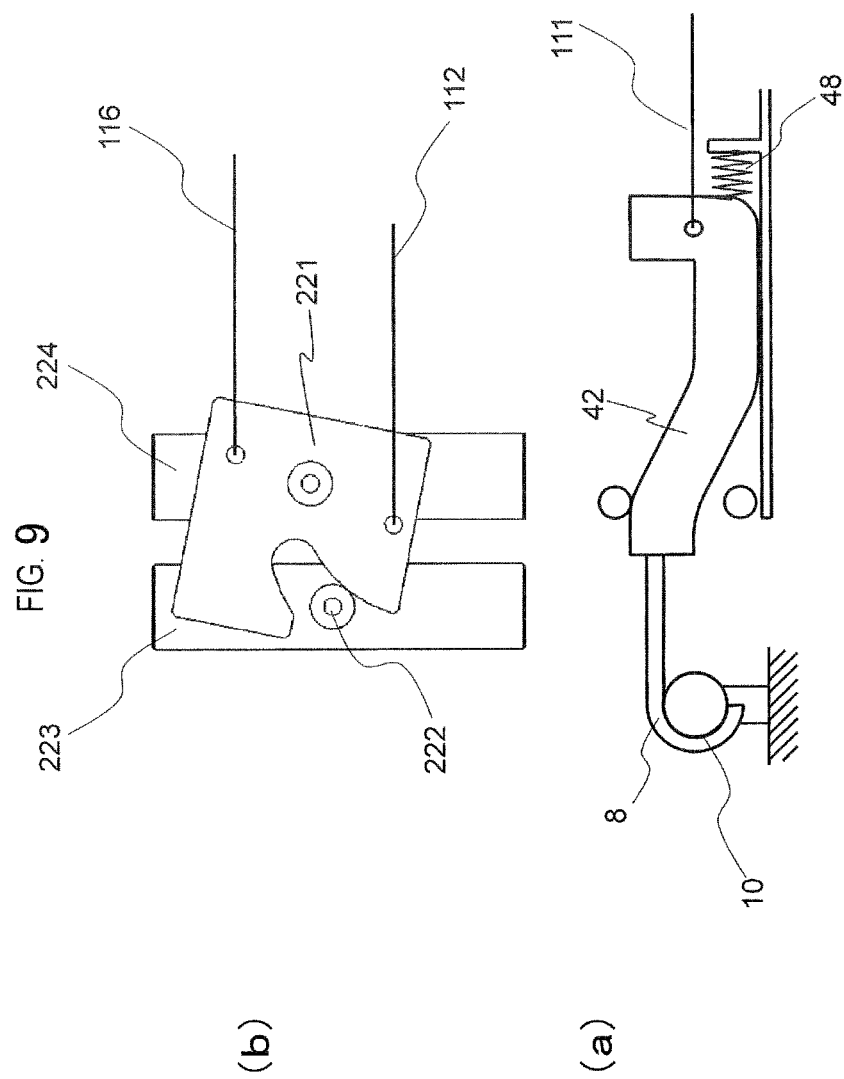
FIG. 9(a) is an explanatory view showing a state where the hook 8 is coupled to the coupling bar 10 through the operation of FIG. 8.
FIG. 9(b) is an explanatory view showing a state where the electric connector 224 and the coupling tools 221 are not coupled to the electric connector 223 and the pins 222 through the operation of FIG. 8.

Accordingly, if the wire A 111 is pulled, the hook 8 of the docking unit 4 of the bed 3 is pulled and is coupled to the coupling bar 10 of the docking unit 5 of the apparatus main body 3 as shown in FIG. 9(*a*), and the docking units 4 and 5 are fixed (Step 603).

Accordingly, the mechanical docking is completed. In addition, since the operation of the electrical docking is not performed yet at this time, the electric connectors 224 and 223 are not coupled together as shown in FIG. 9(*b*).

Figure 10:
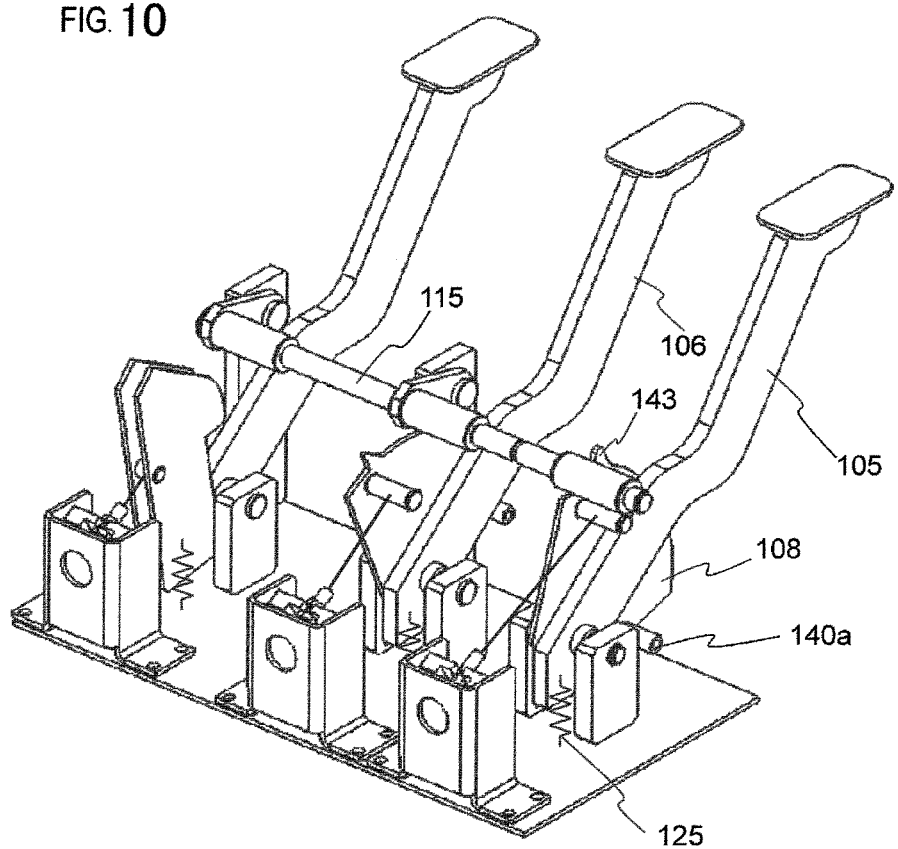
FIG. 10 is a perspective view of a state where only the pedal 105 returns to an initial position from the state of FIG. 8.

Next, if the operator lifts his/her foot off the mechanical docking pedal 105, only the mechanical docking pedal 105 returns to its initial position as shown in FIG. 10 by the force of the spring 125 for pedal return (Steps 604 and 605).

Through the above operation, the locking bar 115 reaches the cutout region 108*b* with the radius r2 (<r1), of the locking plate A 108, whereby the locking bar 115 also comes in contact with the circular-arc region 109*a* of the locking plate B 109 with the same radius r2. Hence, the locking plate B 109 is brought into a state where the locking plate is lockable to locking bar 115.

Figure 11:
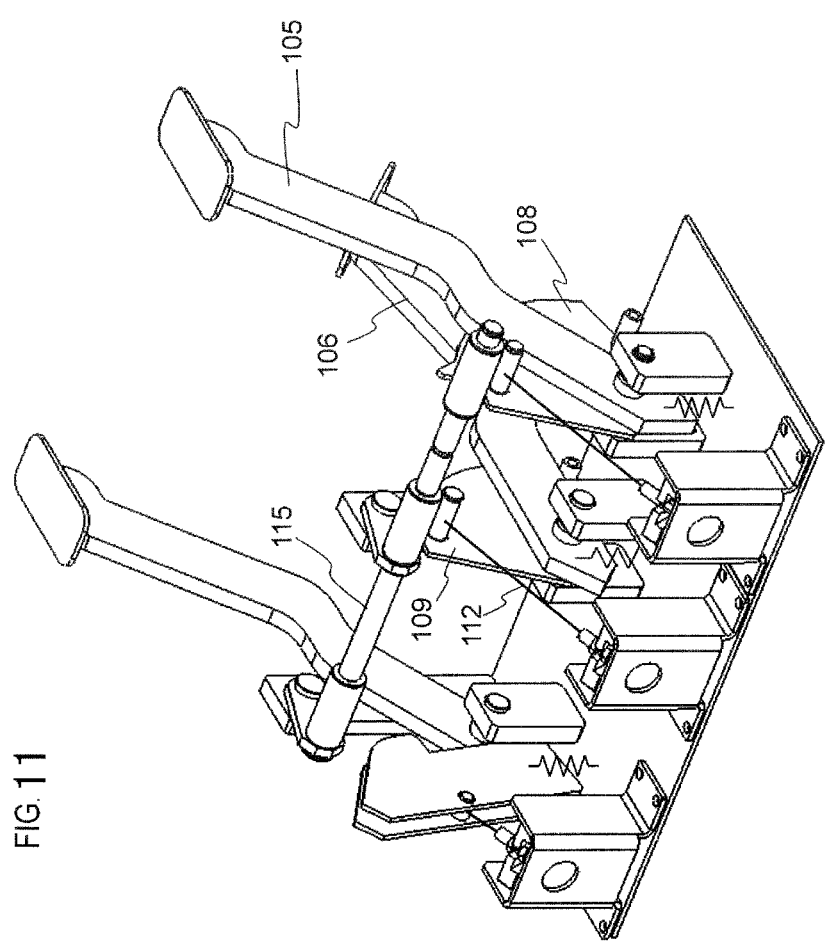
FIG. 11 is a perspective view of a state where a pedal 106 is stepped on from the state of FIG. 10 and the locking plate B 109 is locked.

In this state, if the electrical docking pedal 106 is stepped on as shown in FIG. 11, the pedal-receiving shaft 141*a* is pushed by the pedal 106, the locking plate B 109 is rotated and the wire B 112 is pulled. At this time, the locking bar 115 contacts the circular-arc region 109*a* of the locking plate B 109 with the radius r2. Thus, if the locking plate B 109 is rotated until the protrusion 144 comes to the position of the locking bar 115, and the locking plate B 109 is further rotated, the locking bar 115 rides over the protrusion 144 and reaches the locking region 109*b*.

Unless the locking bar 115 is pushed up by the release plate 117, the locking bar cannot return while riding over the steeply rising side surface shape of the protrusion 144, and as shown in FIG. 11, the locking plate B 109 is locked by the locking bar 115 (Step 606). Since the radius of the locking region 109*b* of the locking plate B 109 is r2 and is equal to the radius r2 of a region that contacts the locking bar 115 of the locking plate A 108 in a locked state, the locking bar 115 contacts the locking plate A 108 and the locking plate B 109 simultaneously, and is brought into a state where the locking bar locks both the locking plates (Step 607).

Figure 12:
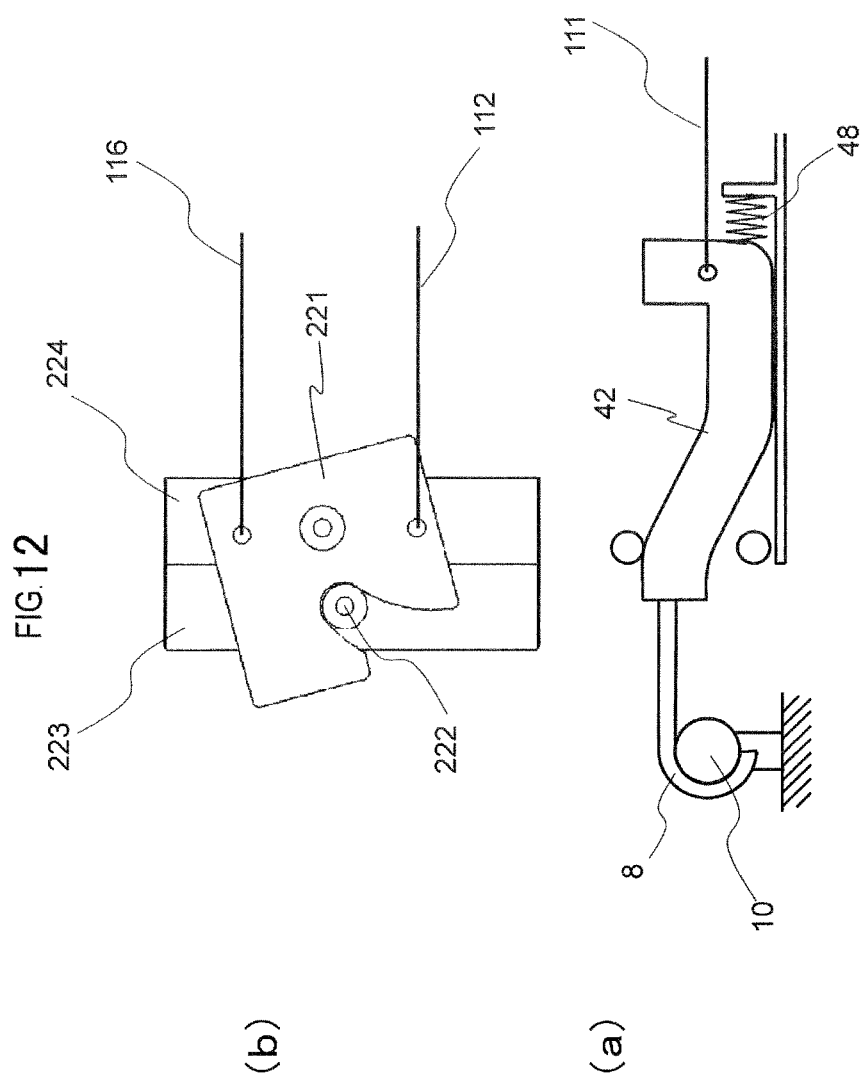
FIG. 12(a) is an explanatory view showing a state where the hook 8 is coupled to the coupling bar 10.
FIG. 12(b) is an explanatory view showing a state where the electric connector 224 of the docking unit 4 is coupled to the electric connector 223 of the docking unit 5 of the apparatus main body 2 by the coupling tools 221 through the operation of FIG. 11.

If the wire B 112 is pulled with the rotation of the locking plate B 109, the coupling tools 221 fixed to the tip of the wire B 112 of FIG. 5 (*b*) are rotated to pull in the pins 222 as shown in FIG. 12(*b*). Accordingly, the electric connector 224 of the docking unit 4 on the bed 3 side and the electric connector 223 of the docking unit 5 on the bed main body 2 side are fitted to each other, and the electrical docking is completed (Step 608). At this time, since the hook 8 is already coupled to the coupling bar 10 in Step 603 as shown in FIG. 12(a), the docking units 4 and 5 are not only mechanically but also electrically coupled to each other.

Figure 13:
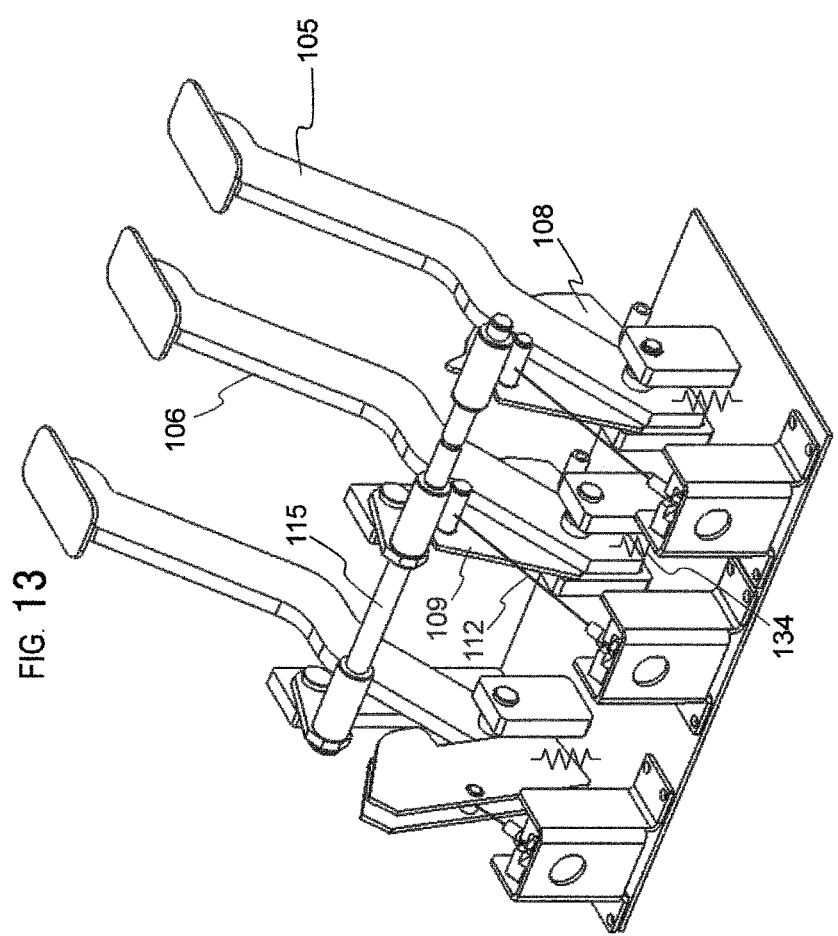
FIG. 13 is a perspective view of a state where only the pedal 106 returns to an initial position from the state of FIG. 12.

Next, if the operator lifts his/her foot off the electrical docking pedal 106, only the electrical docking pedal 106 returns to its initial position as shown in FIG. 13 by the force of the spring 134 for pedal return (Steps 609 and 610).

From the above, the mechanical docking and the electrical docking are performed in this order, and the docking is completed (Step 611).

In the above configuration, when the locking bar 115 rides over the protrusions 143 and 144 of the locking plates A 108 and B 109, a pedal operating force increases and decreases rapidly, and the examiner can obtain an operation feeling. Additionally, when the circular-arc region 108a with the radius r1, of the locking plate A 108 is located at its initial position, the locking bar 115 contacts the locking plate A 108, and the locking bar 115 does not come into contact with the locking plate B 109 anywhere.

That is, even the largest radius r5 of the protrusion 144 among the radius r4, r5, and r2 of the locking plate B 109 is smaller than the radius r1 of the locking plate A 108. For this reason, even if the examiner operates the electrical docking pedal 106, there is no operation feeling because the locking plate B 109 does not come into contact with the locking bar 115 and the pedal can be comfortably stepped on with a small force. Accordingly, even if the electrical docking pedal 106 is stepped on in an unlocked state before operating the mechanical docking pedal 105, locking is not performed, the electrical docking cannot be performed, and the operator can notice an erroneous procedure from a difference in an operation feeling from that during a normal time.

Figure 14:
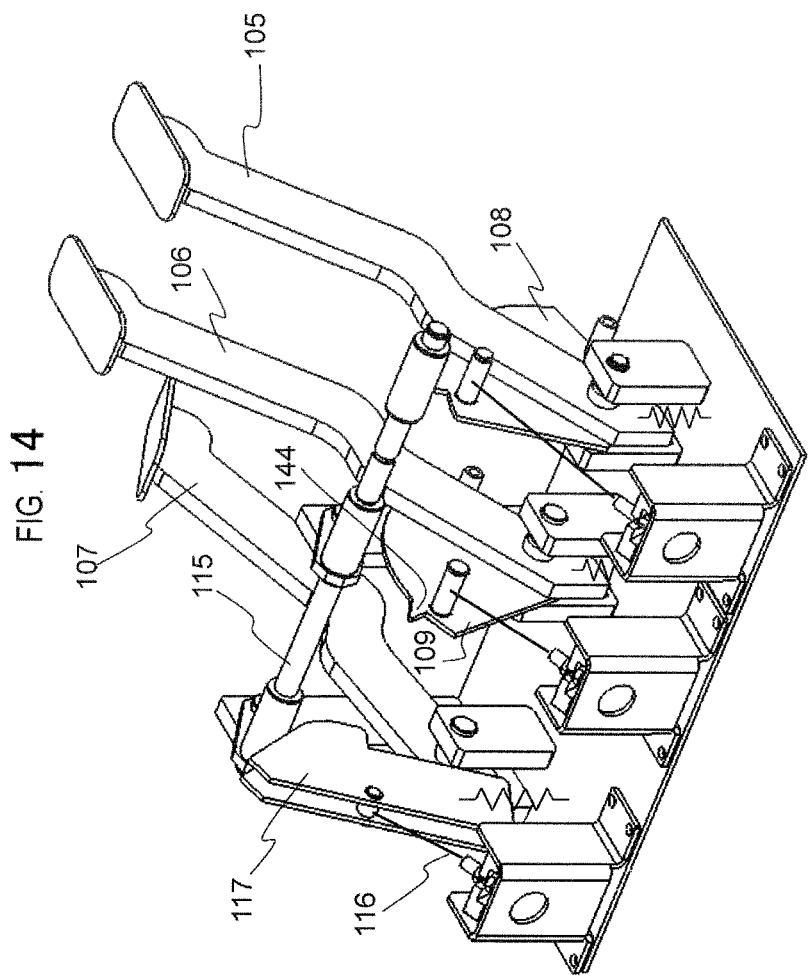
FIG. 14 is a perspective view of a state where the pedal 107 is lightly stepped on from the state of FIG. 13, and the locking plate B 109 is unlocked.

Next, the flow of the docking release will be described with reference to FIG. 7. If the release pedal 107 is stepped on as shown in FIG. 14 in the above-described docking completion state (Step 611), the wire C 116 is pulled by the release plate 117, and the coupling tools 221 are pulled in a release direction (Step 701). Simultaneously, the locking bar 115 is gradually pushed up by the inclined surface of the tip portion of the release plate 117. Accordingly, if the height of the locking bar 115 reaches the radius r5 of the protrusion 144 of the locking plate B 109, the locking of the locking plate B 109 is first released as shown in FIG. 14 (Step 702).

Figure 15:
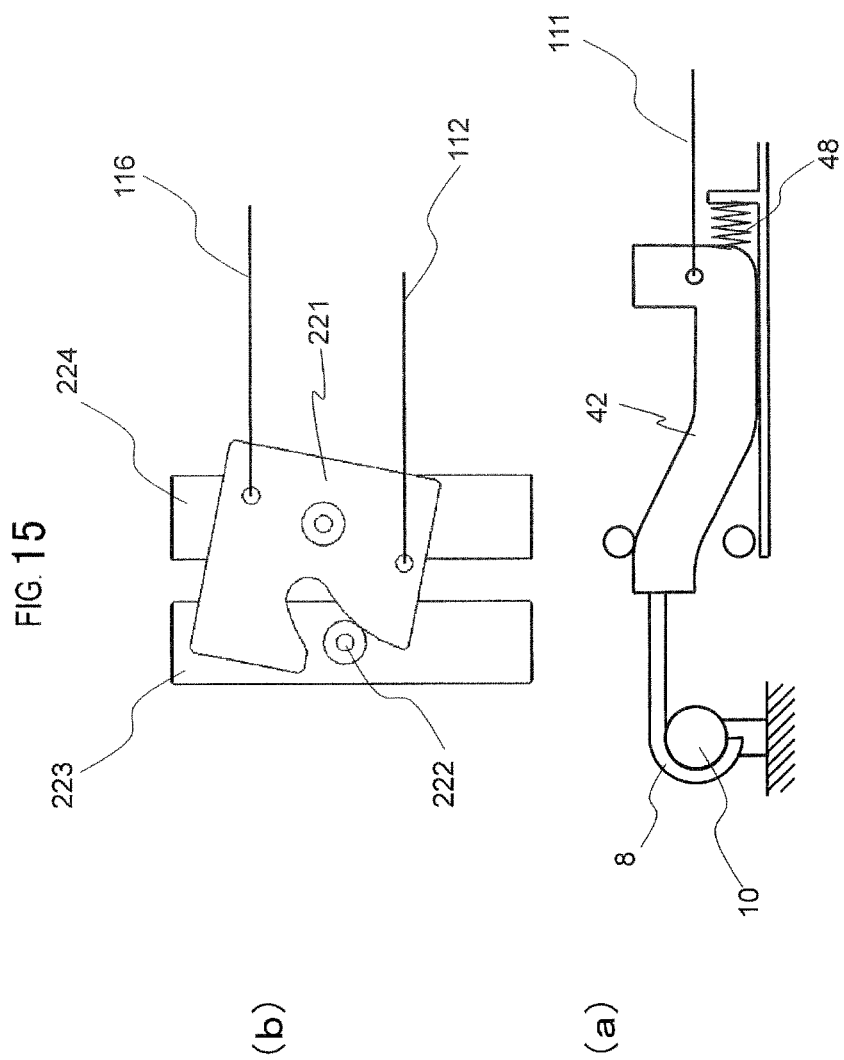
FIG. 15(a) is an explanatory view showing a state where the hook 8 is coupled to the coupling bar 10.
FIG. 15(b) is a view showing a state where the electric connector 224 is decoupled from the electric connector 223 through the operation of FIG. 14.

Accordingly, a force with which the locking plate B 109 pulls the wire B 112 is released and is added to a force with which the wire C 116 pulls the coupling tools 221 in the release direction, and the coupling tools 221 rotates reversely as shown in FIG. 15(b) to push out the pin 222 and releases the coupling between the electric connectors 223 and 224 (Step 703). The electrical docking is first released as described above. At this time, since the locking plate A 108 is still in the locked state, as shown in FIG. 15(a), the hook 8 remains coupled to the coupling bar 10.

Figure 16:
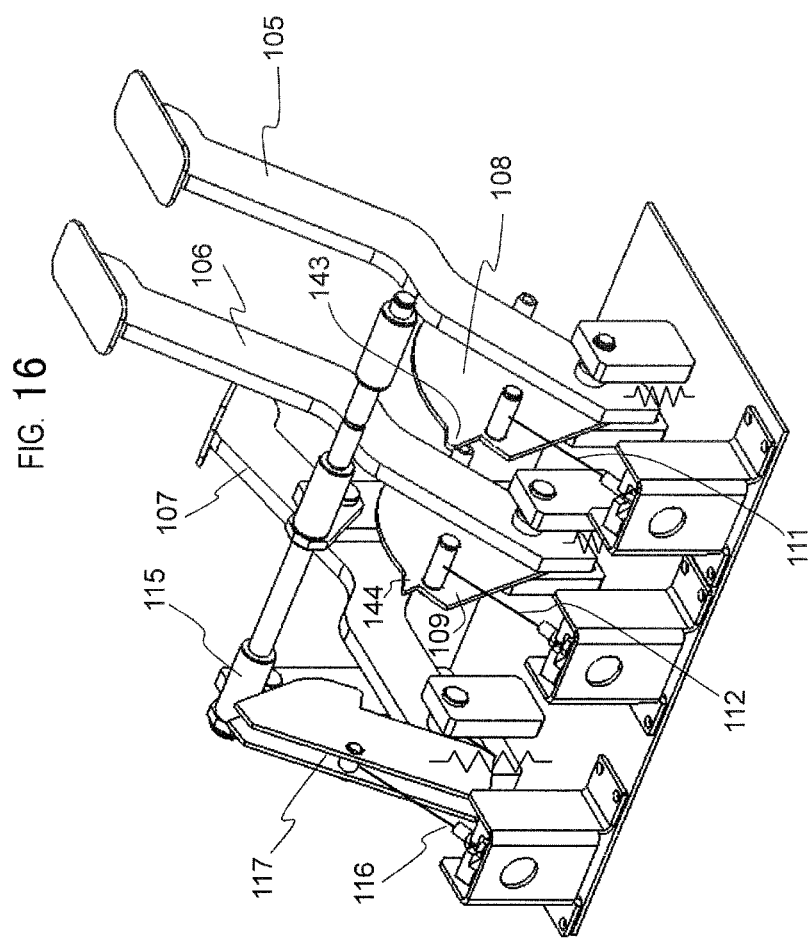
FIG. 16 is a perspective view of a state where the pedal 107 is deeply stepped on from the state of FIG. 14, and the locking plate B 108 is unlocked.

If the examiner further steps on the release pedal 7 deeply as shown in FIG. 16 (Step 704), the release plate 117 further pushes up the locking bar 115, and if the height of the locking bar 115 reaches the height r3 of the tip of the protrusion 143 of the locking plate A, as shown in FIG. 16, the locking of the locking plate A 108 is released (Step 705).

Figure 17:
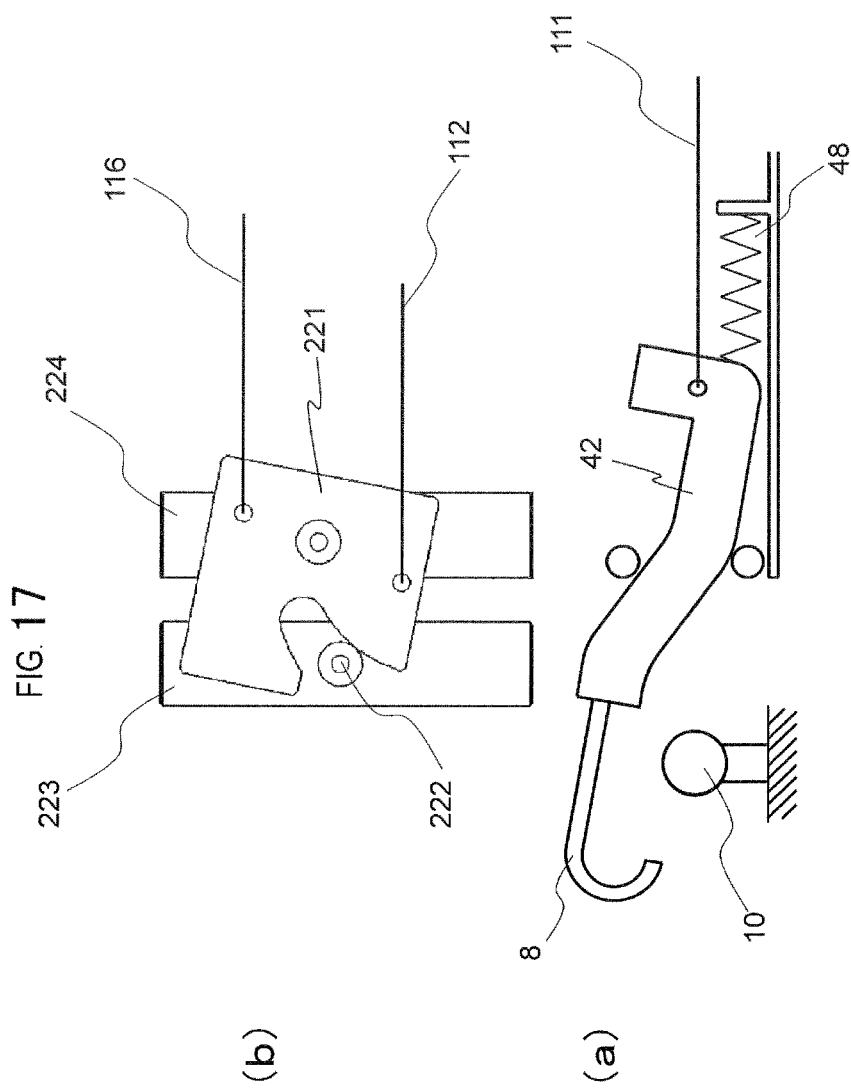
FIG. 17(a) is an explanatory view showing a state where the hook 8 is decoupled from the coupling bar 10 through the operation of FIG. 16.
FIG. 17(b) is an explanatory view showing a state where the electric connector 224 is decoupled from the electric connector 223.

Accordingly, a force with which the locking plate A 108 pulls the wire A 111 is released, and the hook 8 is lifted by the force of the spring 48 arranged at the docking unit 4 as shown in FIG. 17(a), and returns to its initial state (Step 706). Accordingly, the hook 8 is removed from the coupling bar 10, and the mechanical docking is released. Simultaneously, since the wire A 111 is also pulled by the force of the spring 48 in a direction opposite to that during the docking operation, the locking plate A 108 also returns to its initial position. Since the electric connectors 223 and 224 are already decoupled as shown in FIG. 17 (b) in Step 703, both the mechanical docking and the electrical docking are released in Step 703.

If the examiner lifts his/her foot from the release pedal 107, the release pedal 107 returns to its initial state by the pedal return spring 135 (FIG. 3) (Steps 707 to 709), which results in operation completion.

In this way, during release, the electrical docking is first released, and thereafter, the mechanical docking is released. From this, it is possible to avoid a state where the electric connectors 223 and 224 are coupled together in a state where the hook 8 is removed. Accordingly, it is possible to avoid an accident in which the bed 3 may move due to an unexpected operation during the coupling of the electric connectors 223 and 224, and the pins of the connectors may be damaged.

As described above, if the pedal unit 104 of the invention is not operated in a determined order, locking is not caused, and the operation of an erroneous procedure can be prevented. Additionally, unless an examiner operates in the determined order, a pedal can be stepped on with a small force and an operation feeling is not obtained, either. Therefore, an operator can notice when an operating procedure is erroneous.

By using this pedal unit for the coupling between the bed and the apparatus main body, the mechanical docking and the electrical docking can be necessarily performed in this order, and damage of the electric connectors can be prevented. Additionally, during release, the release of the electrical docking and the release of the mechanical docking can be performed in this order, and a phenomenon in which the bed moves while the fitting of the electric connectors remains intact and damages the connectors can be prevented.

Additionally, in the pedal unit of the invention, a pedal returns to its initial position if a foot is lifted from the pedal. Therefore, it is possible to prevent an accident in which, during release, the pedal returns to its initial position unexpectedly and collides with an operator's foot.

Figure 18:
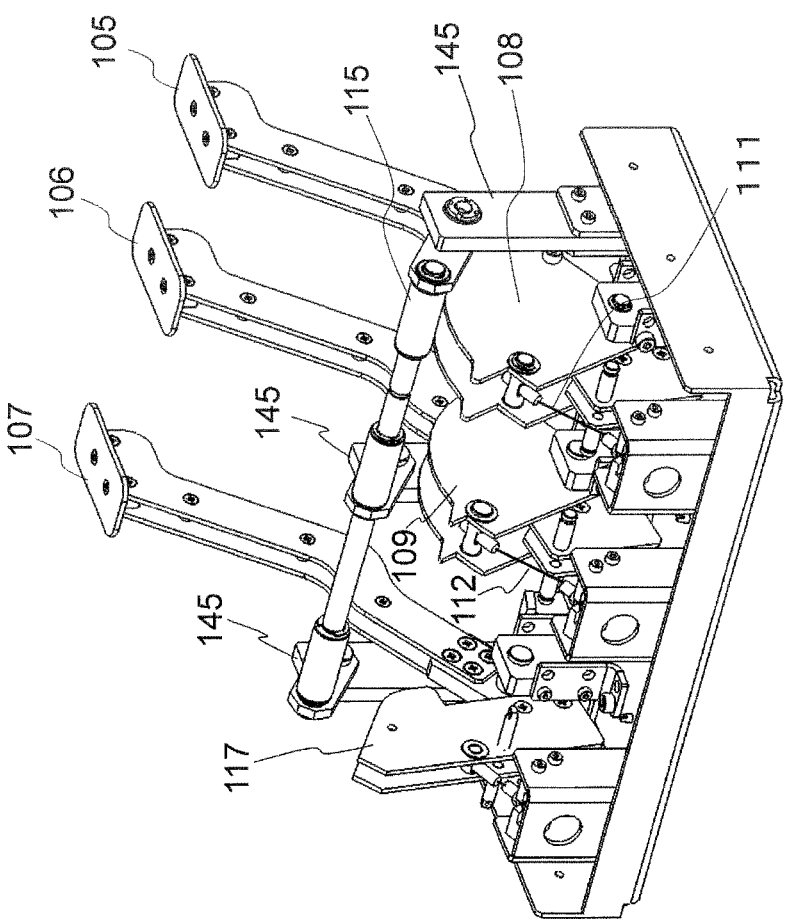
FIG. 18 is a perspective view of a configuration in which the pedal unit of the bed of the embodiments is partially changed.

In addition, the invention is not limited to the shape of FIG. 3, and the shape can be arbitrarily changed. For example, as shown in FIG. 18, it is also possible to make the locking plates A 108 and B 109 into a double structure to improve strength. Additionally, it is also possible to adopt a configuration in which the locking bar 115 is supported by the respectively supporting portions 145 at both ends and the center thereof.

Additionally, the above-described embodiments provide the mechanism in which the pedals 105 and 106 that perform docking are two and are locked in two steps by two plates with different sizes. However, it is also possible to provide a mechanism where pedals that perform docking are three or more and are locked in three or more steps. In this case, three locking plates with different radii are sequentially used.

Here, the structure of the docking units 4 and 5 will be specifically described with reference to FIG. 19 or the like.

Figure 19:
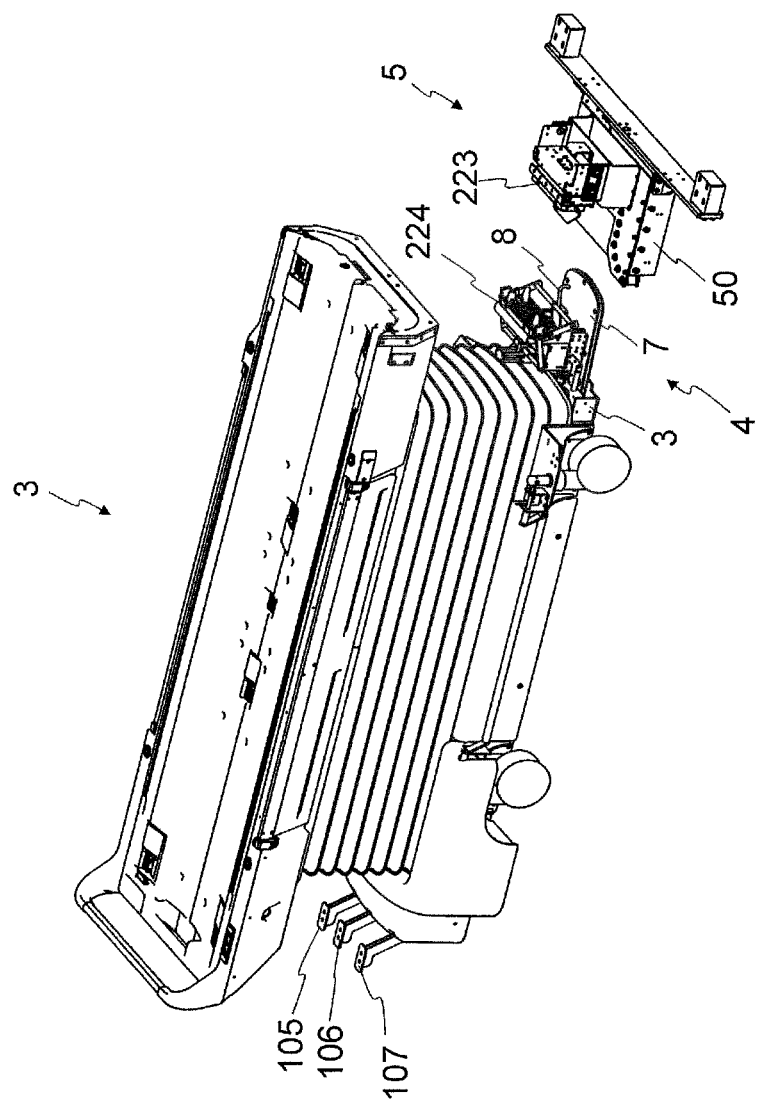
FIG. 19 is a perspective view of the state of the medical imaging apparatus of FIG. 1 where the bed 3 is separated from the apparatus main body 2 and covers are removed from docking units 4 and 5.
Figure 20:
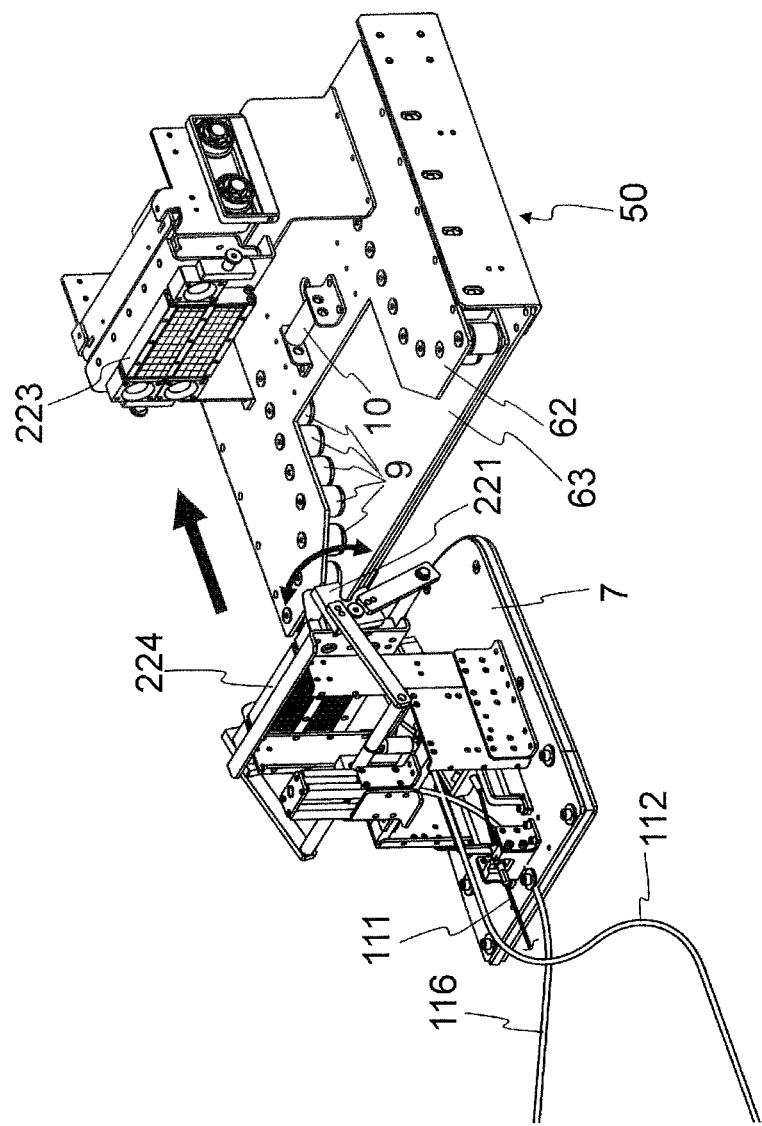
FIG. 20 is an enlarged perspective view of the state of the medical imaging apparatus of FIG. 1 where the covers are removed from the docking units 4 and 5.
Figure 21:
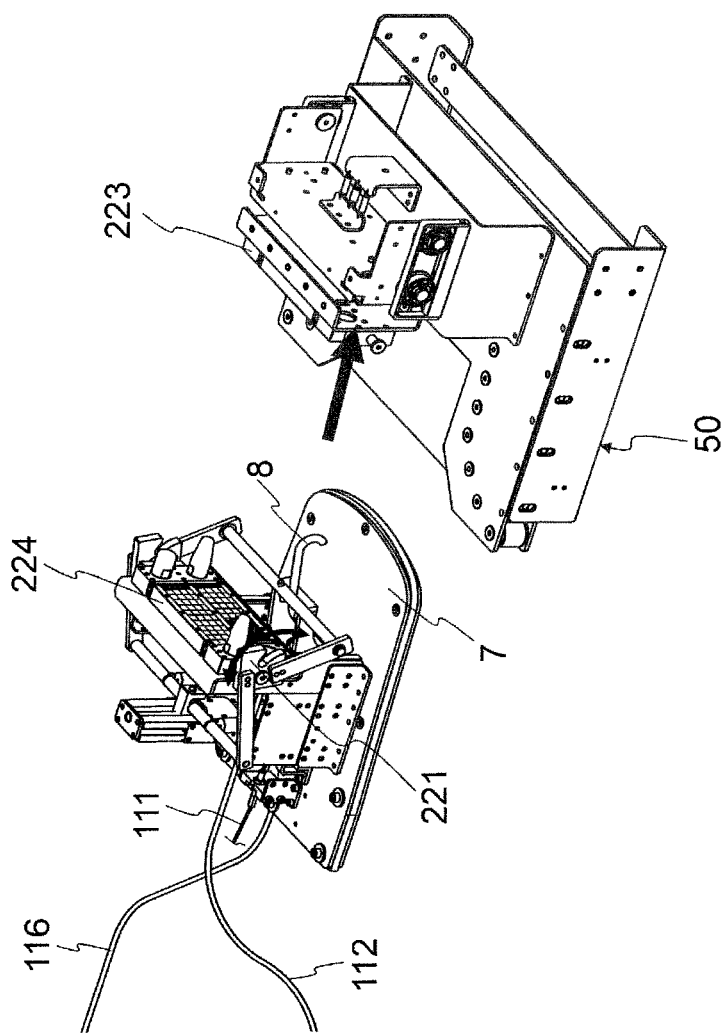
FIG. 21 is an enlarged perspective view of the state of the medical imaging apparatus of FIG. 1 where the covers are removed from the docking units 4 and 5.
Figure 22:
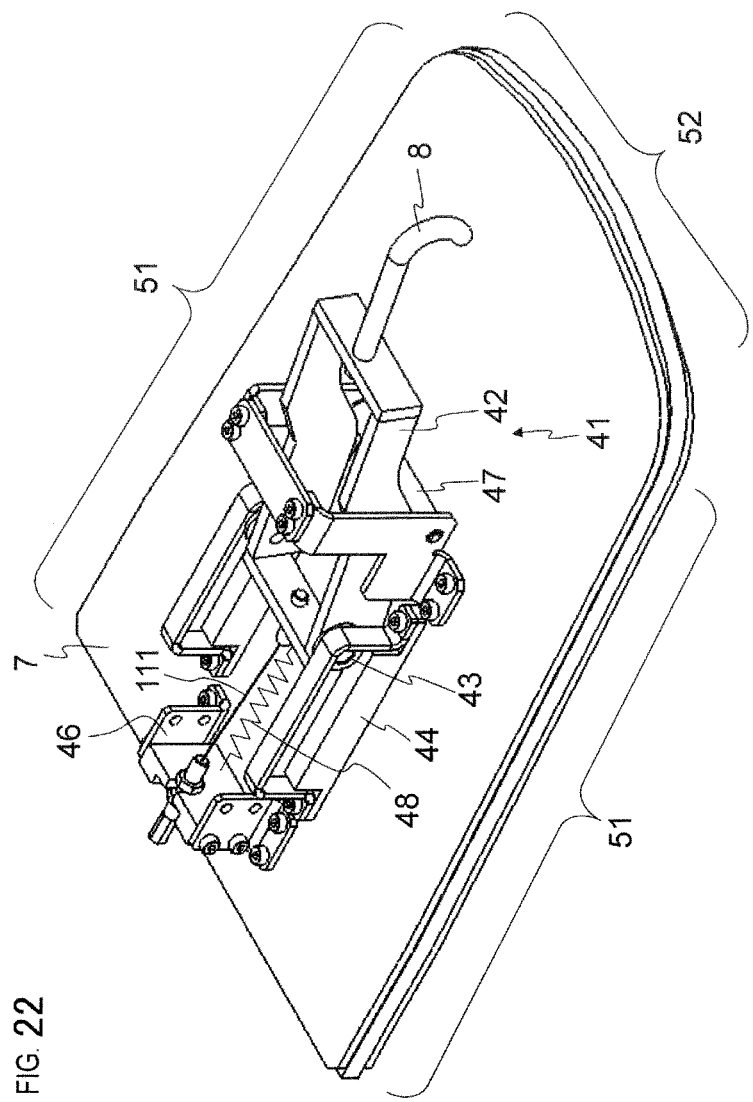
FIG. 22 is an enlarged perspective view of the state of the medical imaging apparatus of FIG. 1 where the cover and an electric connector are removed from docking unit 4.

FIG. 19 is a perspective view of the bed 2 in a state where covers are removed from the docking units 4 and 5, and is a perspective view of the docking unit 5 (the apparatus main body 2 is omitted). FIGS. 20 and 21 are perspective views of the docking units 4 and 5 from which the covers are removed. FIG. 22 is a perspective view in a state where the cover, the electric connector 224, and its drive mechanism are detached from the docking unit 4.

The docking unit 4 on the bed 3 side includes the coupling plate 7 having one end fixed to a frame 34 of the bed 3, the hook 8, and a drive mechanism 41 of the hook 8; the electric connector 224 mounted on the coupling plate 7; and the coupling tools 221. Meanwhile, the docking unit 5 on the apparatus main body 2 side includes the roller unit 50 in which a plurality of rollers 9 are arranged, a coupling bar 10 for coupling with the hook 8, and an electric connector 223 mounted on the roller unit 50. Members that constitute the docking units 4 and 5 are all nonmagnetic members.

The coupling plate 7 of the bed 3 is inserted into the roller unit 50 of the apparatus main body 2, and the bed 3 is fixed in a lateral direction (the width direction of the bed 3) as the coupling plate 7 is sandwiched from side surface directions between the plurality of rollers 9. Additionally, provided is a structure in which the bed 3 is fixed in the long-axis direction thereof as the hook 8 is coupled to the coupling bar 10.

As shown in FIG. 22, the outer shape of the coupling plate 7 is substantially trapezoidal, and has the straight portions 51 on both sides and the curved portion 52 at a tip. By forming both the sides in a linear shape (straight portions 51), the coupling plate 7 can be strongly sandwiched and held by the rollers 9 from both the sides.

The drive mechanism 41 of the hook 8 is fixed at a predetermined position on the coupling plate 7. The drive mechanism 41 of the hook 8 includes a hook supporting portion 42 that is fixed to a base of the hook 8, protrusions 43 that are respectively fixed to both the sides of the hook supporting portion 42, slide guides 44 that slidably guide the protrusions 43 along the axial direction of the bed 3, a wire A 111 that is fixed to a rear end of the hook supporting portion 42, a wire guide 46, and a bar 47 on which the hook supporting portion 42 rides and that lifts the tip of the hook 8. The other end of the wire A 111 is coupled to the pedal 105 at a rear end of the bed 3. Additionally, a spring 48 is arranged between the rear end of the hook supporting portion 42 and the wire guide 46 to bias the hook supporting portion 42 in a direction in which the hook supporting portion is advanced to the front. In addition, although FIG. 22 is a perspective view, the spring 48 is drawn in a simplified manner for convenience of illustration.

Meanwhile, as shown in FIG. 20, the roller unit 50 includes an upper plate 62, a lower plate 63, and the plurality of rollers 9 that are arranged between the upper plate 62 and the lower plate 63 and are rotatably fixed. The coupling plate 7 of the bed 3 is inserted into a space between the upper plate 62 and the lower plate 63, and side surfaces thereof are held by the rollers 9. The coupling bar 10 is fixed to a predetermined position on the upper plate 62. The portion of the upper plate 62 closer to the near side than the coupling bar 10 is cut out. Accordingly, when the coupling plate 7 is inserted into the roller unit 50, the hook 8, its drive mechanism 41, and the electric connector 224 on the coupling plate 7 approach the coupling bar 10 without colliding against the upper plate 62, and are arranged at connectable positions.

When the bed 3 is docked with the apparatus main body 2, an examiner holds the handle portion 11 of the bed 3 to move the bed toward the apparatus main body 2. If the bed 3 approaches the apparatus main body, the coupling plate 7 of the bed 3 contacts the rollers 9 of the roller unit 50 of the apparatus main body 2, the deviations of the position and an angle of the bed 3 with respect to the apparatus main body 2 are corrected, and the tip of the coupling plate 7 is inserted between the rollers 9. If the coupling plate 7 is clamped by four rollers arranged at a position where the coupling plate 7 is clamped among the rollers 9, the coupling plate cannot be inserted anymore; therefore, the movement of the bed 3 stops. This position is a docking position.

If the bed 3 is inserted into the docking position and the examiner operates the pedal 105 to pull the wire A 111, the hook 8 moves in the direction in which the hook is pulled to the rear side (bed 3 side) while descending, and is coupled to the coupling bar 10 on the apparatus main body 2 side. From the above, a mechanical docking operation is completed.

The positional relationship between the electric connectors 223 and 224 in a state (docking position) where the mechanical docking is completed is shown in FIG. 23(a). The electric connector 223 and the electric connector 224 face each other. Although illustration is omitted in FIG. 5, the coupling tools 221 include arms 253 and 254. The wire B 112 is fixed to the coupling tools 221 via the arms 253, and the wire C 116 is fixed to the coupling tools 221 via the arms 254. If the pedal 106 is stepped on, the wire B 112 is pulled, whereby the coupling tools 221 rotate around the shaft 250 as shown in FIG. 23(b). Accordingly, the coupling tools 221 pull in the pins 222 to couple the electric connectors 223 and 224 together.

In contrast, when the bed 3 is separated from the apparatus main body 2, the examiner steps on the pedal 107, and the wire C 116 pulls down the arms 254 and loosens the wire B 112, thereby rotating the coupling tools 221 in the opposite direction to release the coupling, as shown in FIG. 23(c). If the pedal 107 is further stepped on to loosen the wire A 111, the hook 8 is lifted and separated from the coupling bar 10. Accordingly, the electric connectors and the hook 8 are released in this order. Thus, if the examiner holds the handle portion 11 and pulls the bed backward, the bed can be separated from the apparatus main body 2.

REFERENCE SIGNS LIST

1: MEDICAL IMAGING APPARATUS
2: APPARATUS MAIN BODY
3: BED
4: DOCKING UNIT
5: DOCKING UNIT
6: PEDAL
7: COUPLING PLATE
8: HOOK
9: ROLLER
10: COUPLING BAR
31: TOP PLATE
32: TOP PLATE HOLDING PORTION
33: WHEEL
34: FRAME
35: BELLOWS PORTION
42: HOOK SUPPORTING PORTION
43: PROTRUSION
44: SLIDE GUIDE
111: WIRE
46 WIRE GUIDE
47: BAR
48: SPRING
50: ROLLER UNIT
105, 106, 107: PEDAL
108: LOCKING PLATE A
109: LOCKING PLATE B
115: LOCKING BAR
117: RELEASE PLATE
221: COUPLING TOOL

The invention claimed is:
1. A medical imaging apparatus comprising:
a bed that mounts an object;
a main body that images the object, and a pedal unit that is provided at the bed to operate the bed, wherein the pedal unit has first and second pedals, a first plate that rotates through the operation of the first pedal, a second plate that rotates through the operation of the second pedal, and a locking bar that is arranged so as to be capable of being in contact with outer peripheries of the first and second plates, central axes of rotation of the first plate and second plate are coaxial, the first plate has a circular-arc region with a radius r1 from the central axis and a cutout region with a distance r2 from the central axis smaller than the radius r1, at an outer periphery thereof, and the second plate has a circular-arc region with a radius from the central axis equal to the distance r2 at an outer periphery thereof, and the second plate does not come into contact with the locking bar in a state where the circular-arc region of the first plate supports the locking bar through the operation of the first pedal, and the second plate rotates while contacting the locking bar through the operation of the second pedal in a locked state where the locking bar is located in the cutout region of the first plate, wherein one end of a first wire and one end of a second wire are connected to the first and second plates, respectively, and the other ends of the first and second wires are respectively connected to members of the bed to be operated.

2. The medical imaging apparatus according to claim 1, wherein the pedal unit further includes a third pedal, a release plate that rotates through the operation of the third pedal, and a biasing member that applies a force that pushes the locking bar against the outer peripheries of the first and second plates, and the release plate that has rotated through the operation of the third pedal lifts the locking bar against the force of the biasing member to allow the locking bar to move from the cutout region of the first plate to the circular-arc region.

3. The medical imaging apparatus according to claim 1, wherein a protrusion is arranged between the circular-arc region and the cutout region at an outer periphery of the first plate, and the locking bar rides over the protrusion from the circular-arc region and moves to the cutout region when the first plate rotates through the operation of the first pedal.

4. The medical imaging apparatus according to claim 3, wherein a locking region with a distance from the central axis equal to the radius r2 of the circular-arc region, and a protrusion arranged between the circular-arc region and the locking region are provided at an outer periphery of the second plate, and the locking bar rides over the protrusion from the circular-arc region and moves to the locking region when the second plate rotates through the operation of the second pedal.

5. The medical imaging apparatus according to claim 4, wherein the distance of the highest portion of the protrusion of the second plate from the central axis is smaller than the radius r1 of the circular-arc region of the first plate.

6. The medical imaging apparatus according to claim 5, wherein the pedal unit further includes a third pedal, a release plate that rotates through the operation of the third pedal, and a biasing member that applies a force that pushes the locking bar against the outer peripheries of the first and second plates, and the release plate that has rotated through the third pedal gradually lifts the locking bar against the force of the biasing member and the release plate unlocks the second plate and the first plate in this order.

7. The medical imaging apparatus according to claim 2, wherein one end of a third wire is fixed to the release plate and the other end of the third wire is connected to a member of the bed, the operation of which is to be released.

8. The medical imaging apparatus according to claim 1, wherein the bed is structured to be detachable from the main body, and a coupling member that mechanically couples the bed and the main body is connected to the other end of the first wire, and a coupling member that electrically connects the bed and the main body is connected to the other end of the second wire.

9. A medical imaging apparatus comprising:
a bed that mounts an object;
a main body that images the objects, and
a pedal unit that is provided at the bed to operate the bed, wherein the pedal unit has first and second pedals, a first plate that rotates through the operation of the first pedal, a second plate that rotates through the operation of the second pedal, and a locking bar that is arranged so as to be capable of being in contact with outer peripheries of the first and second plates, central axes of rotation of the first plate and second plate are coaxial, the first plate has a circular-arc region with a radius r1 from the central axis and a cutout region with a distance r2 from the central axis smaller than the radius r1, at an outer periphery thereof, and the second plate has a circular-arc region with a radius from the central axis equal to the distance r2 at an outer periphery thereof, and the second plate does not come into contact with the locking bar in a state where the circular-arc region of the first plate supports the locking bar through the operation of the first pedal, and the second plate rotates while contacting the locking bar through the operations of the second pedal in a locked state where the locking bar is located in the cutout region of the first plate, and wherein the first pedal returns to a predetermined initial position without interlocking with the first plate in a locked state where the locking bar is located in the cutout region of the first plate.

10. A medical imaging apparatus comprising:
a bed that mounts an object;
a main body that images the object, and
a pedal unit that is provided at the bed to operate the bed, wherein the pedal unit has first and second pedals, a first plate that rotates through the operation of the first pedal, a second plate that rotates through the operation of the second pedal, and a locking bar that is arranged so as to be capable of being in contact with outer peripheries of the first and second plates, central axes of rotation of the first plate and second plate are coaxial, the first plate has a circular-arc with a radius r1 from the central axis and a cutout region with a distance r2 from the central axis smaller that the radius r1, at an outer periphery thereof, and the second plate has a circular-arc region with a radius from the central axis equal to the distance r2 at an outer periphery thereof, and the second plate does not come into contact with the locking bar in a state where the circular-arc region of the first plate supports the locking bar through the operation of the first pedal, and the second plate rotates while contacting the locking bar through the operation of the second pedal in a locked state where the locking bar is located in the cutout region of the first plate, and wherein one end of the first wire and one end of the second wire are connected to the first and second plates, respectively, and the other ends of the first and second wires are respectively connected to members of the bed to be operated, wherein the apparatus main body is a magnetic resonance imaging apparatus.

11. A bed for a medical imaging apparatus including a pedal unit for operation, wherein the pedal unit has first and second pedals, a first plate that rotates through the operation of the first pedal, a second plate that rotates through the operation of the second pedal, and a locking bar that is arranged so as to be capable of being in contact with outer peripheries of the first and second plates, central axes of rotation of the first plate and second plate are coaxial, the first plate has a circular-arc region with a radius r1 from the central axis and a cutout region with a distance r2 from the central axis smaller than the radius r1, at an outer periphery thereof, and the second plate has a circular-arc region with a radius from the central axis equal to the distance r2 at an outer periphery thereof, and the second plate does not come into contact with the locking bar in a state where the circular-arc region of the first plate supports the locking bar through the operation of the first pedal, and the second plate rotates while contacting the locking bar through the operation of the second pedal in a locked state where the locking bar is located in the cutout region of the first plate, wherein one end of a first wire and one end of a second wire are connected to the first and second plates, respectively, and the other ends of the first and second wires are respectively connected to members of the bed to be operated.

12. A pedal unit comprising:

first and second pedals;

a first plate that rotates through the operation of the first pedal;

a second plate that rotates through the operation of the second pedal; and a locking bar that is arranged so as to be capable of being in contact with outer peripheries of the first and second plates, wherein central axes of rotation of the first plate and second plate are coaxial, the first plate has a circular-arc region with a radius r1 from the central axis and a cutout region with a distance r2 from the central axis smaller than the radius r1, at an outer periphery thereof, and the second plate has a circular-arc region with a radius from the central axis equal to the distance r2 at an outer periphery thereof, and the second plate does not come into contact with the locking bar in a state where the circular-arc region of the first plate supports the locking bar through the operation of the first pedal, and the second plate rotates while contacting the locking bar through the operation of the second pedal in a locked state where the locking bar is located in the cutout region of the first plate, wherein the pedal unit further includes a third pedal, a release plate that rotates through operation of the pedal, and a biasing member that applies a force that pushes the locking bar against the outer peripheries of the first and second plates, and the release plate that has rotated through the operation of the third pedal lifts the locking bar against the force of the biasing member to allow the locking bar to move from the cutout region of the first plate to the circular-arc region.

* * * * *